United States Patent [19]

Foreman et al.

[11] Patent Number: 5,444,531
[45] Date of Patent: Aug. 22, 1995

[54] SENSOR WITH LED CURRENT CONTROL FOR USE IN MACHINES FOR WASHING ARTICLES

[75] Inventors: Donald S. Foreman, Fridley; David Kubisiak, Chanhassen, both of Minn.

[73] Assignee: Honeywell Inc., Minneapolis, Minn.

[21] Appl. No.: 246,895

[22] Filed: May 20, 1994

[51] Int. Cl.⁶ .......................................... G01N 21/53
[52] U.S. Cl. .................... 356/341; 356/339; 68/12.27
[58] Field of Search ............... 356/339, 442, 70, 341; 134/113; 68/12.02, 12.27; 250/574

[56] References Cited

U.S. PATENT DOCUMENTS

| | | |
|---|---|---|
| 3,114,253 | 12/1963 | Morey et al. . |
| 3,662,186 | 5/1972 | Karklys . |
| 3,800,147 | 3/1974 | Shea et al. ............... 356/442 |
| 3,870,417 | 3/1975 | Bashark . |
| 3,888,269 | 6/1975 | Bashark . |
| 3,892,485 | 7/1975 | Merritt et al. ............ 356/339 |
| 4,110,044 | 8/1978 | Pettersson et al. ........ 250/574 |
| 4,193,692 | 3/1980 | Wynn . |
| 4,257,708 | 3/1981 | Fukuda . |
| 4,537,510 | 8/1985 | Takahasi ................... 356/435 |
| 4,619,530 | 10/1986 | Meserol et al. . |
| 4,906,101 | 3/1990 | Lin et al. . |
| 4,999,514 | 3/1991 | Silveston . |
| 5,048,139 | 9/1991 | Matsumi et al. . |
| 5,140,168 | 8/1992 | King . |
| 5,172,572 | 12/1992 | Ono . |
| 5,291,626 | 3/1994 | Molnar et al. ............ 356/339 |

FOREIGN PATENT DOCUMENTS 8200836 8/1982 European Pat. Off. .
2068419A 8/1981 United Kingdom .

OTHER PUBLICATIONS

Article titled "A new Control Device for Washing Machines Using a Microcomputer and Detectors", by Matsuo and Taniguchi, (Sep./Oct. 1984).

*Primary Examiner*—Richard A. Rosenberger
*Attorney, Agent, or Firm*—William D. Lanyi

[57] ABSTRACT

A plurality of fluid condition sensors are combined together to provide a sensor cluster that senses turbidity, temperature, conductivity and the movement of a ferromagnetic object. The plurality of sensors are attached to a substrate and encapsulated, by an overmolding process, with a light transmissive and fluid impermeable material. The sensor cluster can be disposed at numerous different locations within a body of fluid and does not require a conduit to direct the fluid to a particular location proximate the sensor. In a preferred embodiment of the present invention, a circuit is provided which monitors the signal strength of first and second light sensitive components to determine turbidity and, in addition, those signal strengths are also used to advantageously determine the most efficient magnitude of current necessary to drive a light source, such as a light emitting diode. By controlling the current to a light emitting diode as a function of the strength of light signal received by first and second light sensitive components, the turbidity sensor can be operated at a more efficient and effect level.

10 Claims, 14 Drawing Sheets

SENSOR WITH LED CURRENT CONTROL FOR USE IN MACHINES FOR WASHING ARTICLES

BACKGROUND OF THE INVENTION

FIELD OF THE INVENTION

The present invention is generally related to sensors for use in machines for washing articles and, more particularly, to a sensor platform, or cluster, which contains and protects a series of parameter sensing components and is attachable in various places within a dishwasher or washing machine for monitoring the condition of the liquid used by the machine.

DESCRIPTION OF THE PRIOR ART

U.S. Pat. No. 5,140,168, which issued to King on Aug. 18, 1992, discloses a turbidimeter signal processing circuit which uses alternating light sources. The turbidimeter includes a housing which has a cavity with an inlet through which fluid flows. Two emitters are alternately driven by an alternating signal having a given frequency to transmit modulated light beams through the fluid. Two detectors produce signals representing the intensity of scattered and unscattered light within the fluid. Each of these detector signals is processed to measure the level of the signal component at the given frequency. Such processing includes filtering and phase demodulating the detector signals to produce a signal indicative of the levels of the component signals at the given frequency. The turbidity is calculated from the signal levels measured as each emitter is excited.

U.S. Pat. No. 3,888,269, which issued to Bashark on Jun. 10, 1975, describes a control system for a dishwasher. The dishwasher has a single control pushbutton adapted to perform a multiplicity of different dishwashing and dishtreating operations. It includes an improved automatic control which has the capability to determine an optimum treatment of the dishes in the dishwasher based on the condition of the dishes when they are in the dishwasher.

U.S. Pat. No. 3,870,417, which issued to Bashark on Mar. 11, 1975, discloses a sensor for a dishwasher. It describes a method and apparatus for determining the condition of a liquid, such as a dishwashing liquid, including means for determining the turbidity of the liquid and means for determining a preselected amount of evaporation of the liquid so as to determine a dryness condition. Means are provided for directing light radiation upward into the liquid and for sensing the light radiation reflected either from solids carried by the liquid to provide a turbidity determination or reflected from the underside of the upper surface of the liquid to provide a dryness determination.

U.S. Pat. No. 5,172,572, which issued to Ono on Dec. 22, 1992, discloses an automatic washing apparatus for washing dirty things in a washing tank to which washing liquid is supplied. The apparatus comprises a light emitting element for emitting light to the washing liquid which has passed through the washing tank. It also comprises a first light receiving element for receiving a linear light beam which travels through the washing liquid along the optical axis of the light emitting element. Furthermore, it comprises a second light receiving element for receiving scattered light which travels through the washing liquid in directions deviated from the optical axis of the light emitting element, wherein washing conditions are controlled in accordance with the quantity of light received by the first light receiving element and the quantity of light received by the second light receiving element.

U.S. Pat. No. 3,662,186, which issued to Karklys on May 9, 1972, describes an electronic control circuit for appliances. The control for a multiple function apparatus, such as an appliance, utilizes an electronic clock, or timer, electronic program circuitry and digital circuitry to select and control the functions to be performed. The electronic program circuitry has a plurality of bi-stable circuits, one portion controlling a series of steps repeated in each of several subcycles and the other portion controlling the sequence of subcycles. The second portion may be preset to establish a desired operating program. The digital circuitry is responsive to the condition of the bistable program circuits and to the clock to control the operation of the appliance.

U.S. Pat. No. 5,291,626, which issued to Molnar et. al. on Mar. 8, 1994, discloses a machine for cleansing articles. The machine, such as a dishwasher, incorporates a device for measuring the turbidity of at least partially transparent liquid. The device includes a sensor for detecting scattered electromagnetic radiation, regardless of polarization, and a sensor for detecting transmitted electromagnetic radiation.

U.S. patent application No. 08/053,042 which was filed by Kubisiak et. al. on Apr. 26, 1993 and assigned to the assignee of the present application describes a turbidity sensor that is provided with a light source and a plurality of light sensitive components which are disposed proximate a conduit to measure the light intensity directly across the conduit from the light source and at an angle therefrom. The conduit is provided with a plurality of protrusions extending radially inward from the walls of the conduit to discourage the passage of the air bubbles through the light beam of the sensor. The direct light beam and scattered light are compared to form a relationship that is indicative of the turbidity of the liquid passing through the conduit. The rate of change of turbidity is provided as a monitored variable. The technique referred to as the delta-sigma analog-to-digital conversion method is described in significant detail in the Kubisiak et. al. application. The Kubisiak et. al. application described above is expressly incorporated by reference herein.

U.S. Pat. No. 4,906,101, which issued to Lin et. al. on Mar. 6, 1990, describes a turbidity measuring device for measuring turbidity in static or dynamic streams, wherein the fluid has up to 8,500 ppm solids and at a depth of up to 8 inches. The device contains a high intensity light source, a means for controlling the wavelength of the transmitted light to between 550–900 nm to filter color variables in the stream. It also comprises a photosensor that is aligned with the viewing means for picking up the light transmitted through the streams.

U.S. Pat. No. 5,048,139, which issued to Matsumi et. al. on Sep. 17, 1991, discloses a washing machine with a turbidimeter and a method of operating the turbidimeter. The machine uses a turbidimeter to measure turbidity of cleaning water for controlling the duration of its washing and cleaning cycles. Quality of this control is improved by taking measurements when the water flow is weak so that the effects of foams are negligible and waiting until turbidity drops at the beginning of the cycle to detect the initial value used in subsequent steps.

U.S. Pat. No. 4,999,514, which issued to Silveston on Mar. 12, 1991, discloses a turbidity meter with parameter selection and weighting. The meter has a sensory unit which is supported in a fluid under test with a light source and at least two light sensors supported so that one light sensor is in line with the source to receive transmitted light and the remaining sensor or sensors are arranged to receive light that is scattered by the fluid. Both the source and the sensors have flow forming chambers connected to a source of pressurized fluids so that a thin layer of this fluid is caused to flow over lenses of the source and sensors to prevent deposition of material from the fluid under test.

U.S. Pat. No. 4,619,530, which issued to Meserol et. al. on Oct. 28, 1986, describes a cuvette with an integral optical elements and electrical circuit with photoemissive and photosensitive elements in intimate optical contact with the optical elements. The combination of a cuvette for receiving a medium undergoing change in optical characteristics which change modifies the energy level of array of energy passing through the medium and wherein the cuvette is provided with integrally formed first and second array modifying optical means such as collimating and collecting lens. The first ray modifying optical means receives and modifies the ray in a first manner, such as be culmination, and them transmits the ray into the medium. The second ray modifying optical means receives and modifies the ray in a second manner, such as by collection, upon the ray passing through the medium and transmits the ray from the cuvette. An electrical circuit includes photoemissive and photosensitive means such as a photoemitter and photodetector, wherein the photoemissive means is in intimate optical contact with the first ray modifying optical element of the cuvette and wherein the photosensitive means is in optical contact with the second ray modifying means.

U.S. Pat. No. 4,193,692, which issued to Wynn on Mar. 18, 1980 describes a method and apparatus for the optical measurement of the concentration of a particulate in a fluid. An optical concentration measuring apparatus and method which provides an output signal which is a substantially linear function of the concentration is disclosed in the Wynn patent. The apparatus includes a chamber for containing a fluid sample and a source of optical radiation which develops a beam which is transmitted through the chamber and through the sample. A first photoelectric cell is disposed to receive the transmitted beam for generating an electrical signal commensurate with the intensity of the beam after passage through the chamber and the fluid sample. A second photoelectric cell which is disposed at a selected angle with respect to the direct beam for providing an electric signal commensurate with the light scattered in a direction corresponding to the selected signal is also provided. The signal commensurate with the scattered beam and the signal commensurate with the direct beam are applied to a single processor which develops a ratio of these signals. One of the signals is multiplied by a constant value. The method allows the constant value to be selected so that a signal from the signal processor is substantially linear with the particulate concentration.

Known turbidity sensing devices operate under one of two conditions. First, a tubular structure is provided to cause a fluid to flow past a predetermined detection zone. As the fluid flows through the conduit, a light is directed through the fluid and received by one or more light sensitive components disposed across the diameter of the conduit and, occasionally, at an angle to the line extending between the light emitting means and the light sensitive component which is disposed on an opposite side of the conduit from the light emitting means. An alternative method of utilizing a turbidity sensor is to provide a fluid connection tank, or well, which contains a sample portion of the fluid to be monitored. The light emitting and light sensitive components are arranged at sides of the well to direct a light through the fluid. Both of these known methods of applying a turbidity sensor have a common disadvantage. They require some means for directing or transporting fluid to the operative detection zone of the sensor. This requirement limits their adaptability in certain applications.

In addition to the disadvantage described above, known turbidity sensors are not easily adapted to incorporate a plurality of other sensors, such as a temperature sensor, a conductivity sensor and a position detector that permits the detection of movement of a preselected component, such as a rotatable washer arm. In modern apparatus for cleansing articles, such as dishwashers or clothes washers, the control circuitry can benefit from information relating to the turbidity of the washing fluid, the conductivity of the washing fluid, the temperature of the washing fluid and the movement of a rotatable member such as a water spray arm. It would therefore be beneficial if a single sensor module, or cluster, could be provided which is able to sense the turbidity, the temperature and the conductivity of the washing fluid and also determine whether or not a moveable object is properly functioning. It would be further beneficial if such a cluster of sensors could be provided as a single item which is disposable in a multiplicity of locations within the appliance without the need for providing tubing, conduits or fluid containing reservoirs. It would also be beneficial if a cluster of sensors could monitor the parameters of a device, such as its temperature, water turbidity level, water conductivity level and the position of a moveable object, in parallel with the control of an appliance by another microprocessor and make the measurements of the parameters available on call by the other host microprocessor. In this way, the host microprocessor would not be burdened by the necessity of waiting while the measurements were taken.

SUMMARY OF THE INVENTION

The liquid condition sensor of the present invention comprises a substrate having a first planar surface. The substrate has a plurality of electrically conducting portions disposed on the first planar surface. In other words, the substrate can be in the general form of a printed circuit board with a plurality of conductive runs disposed on its surface. A preferred embodiment of the present invention also comprises a means, attached to the substrate, for directing a beam of light energy along a first line in a direction parallel to the first planar surface of the substrate. It also comprises a first light sensitive means, attached to the substrate, for receiving light energy directly from the directing means. The first line intersects the first receiving means and the light source. The first receiving means provides a first signal which is representative of the light intensity impinging on the first receiving means. The present invention further comprises a second light sensitive means which is attached to the substrate. The second light sensitive means is provided for receiving scattered light from the directing means along a second line which is parallel to the first planar surface. The second line is perpendicular to the first line in a preferred embodiment of the present invention. The second line intersects the second receiving means and the second receiving means provides a second signal representative of the light intensity impinging on the second receiving means. The light directing means, the first receiving means and the second receiving means are connected in electrical communication with a first one of the plurality of electrically conductive portions of the substrate. In addition, the present invention comprises a means for comparing the first and second signals. This comparing means is connected in signal communication with the first and second receiving means.

The substrate of the present invention can be disposed within a pump housing of a dishwasher. In addition, the present invention further comprises a first means for measuring the electrical conductivity of the liquid proximate the first planar surface of the substrate. The measuring means is connected in electrical communication with a second one of the plurality of electrically conductive portions of the substrate. The first measuring means comprises two electrodes having a known surface area and extending from the first planar surface and spaced apart from each other by a predetermined distance.

A particularly preferred embodiment of the present invention also comprises a second means for measuring the temperature of the liquid proximate the first planar surface of the substrate. The second measuring means is connected in electrical communication with a third one of the plurality of electrically conductive portions on the substrate.

A preferred embodiment of the present invention further comprises a magnetically sensitive component for detecting the presence of a ferromagnetic object within a predetermined detection zone proximate the substrate. The magnetically sensitive component is connected in electrical communication with a fourth one of the plurality of electrically conductive portions of the substrate. In a particularly preferred embodiment of the present invention, the magnetically sensitive component comprises a magnetoresistive element.

A particularly preferred embodiment of the present invention further comprises a plurality of electrical conductors extending from a second planar surface of the substrate, wherein the second planar surface of the substrate is disposed on an opposite side of the substrate from the first planar surface. The plurality of electrical conductors are connected in signal communication with the first, second, third and fourth electrically conductive portions of the substrate. The substrate, the light directing means, the first light sensitive means and the second light sensitive means are encapsulated within a light transmissive and liquid impermeable substance.

One embodiment of the present invention comprises a turbidity sensor which regulates the current flowing to the light emitting diode as a function one or more of the first and second signals provided by the first and second light sensitive components, 36 and 40. The sensor in that embodiment comprises a light source that is disposed to transmit a beam of light in a direction along a first line through the detection zone. It also comprises a first light sensor that is disposed to receive light transmitted along the first line. The first light sensor provides a first signal representing the intensity of light impinging on it. In addition, a second light sensor is disposed to receive light scattered along the second line and provide a second signal representing the intensity of the scattered light. A regulator is provided for controlling the intensity of the light emanating from the light source as a function of a preselected one of the first and second signals. Alternative embodiments of the present invention can regulate the current through the light emitting diode as a function of the first light sensitive component that receives transmitted light or the second light sensitive component that receives scattered light. Alternatively, the regulator for controlling the current flowing through the light emitting diode can regulate the current as a function of both the first and second signals emanating from the first and second light sensitive components, respectively. In an embodiment which utilizes both signals, the higher of the two signals is used.

BRIEF DESCRIPTION OF THE DRAWINGS

The present invention will be more fully understood from a reading of the Description of the Preferred Embodiment in conjunction with the drawings, in which.

DESCRIPTION OF THE PREFERRED EMBODIMENT

Figure 1:
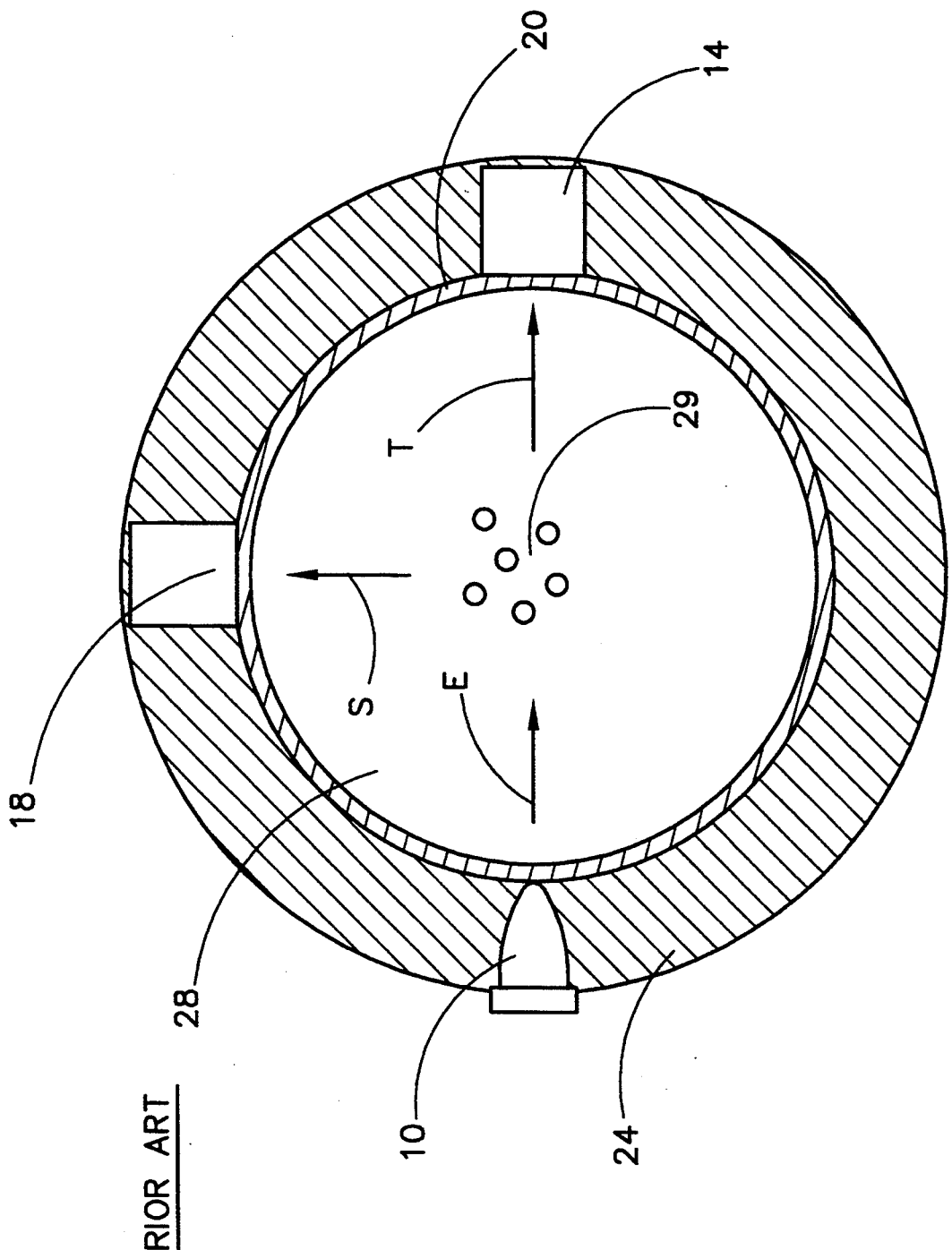
FIG. 1 is a cross sectional view of a turbidity sensor made in accordance with techniques known to those skilled in the art.

Throughout the Description of the Preferred Embodiment, like components will be identified by like reference numerals.

FIG. 1 illustrates a cross section view of one type of turbidity sensor arrangement known to those skilled in the art. A light source 10, such as a light emitting diode, is arranged relative to a conduit 20 in order to permit the light source 10 to direct a beam of light into a fluid 28 within the conduit 20. This emitted light is represented by arrow E in FIG. 1. A first light sensitive component 14 is attached to the conduit 20 at a diametrically opposite position relative to the light source 10. Light transmitted from the light source 10 to the first light sensitive component 14 is represented by arrow T.

With continued reference to FIG. 1, a second light sensitive component 18 is attached to the conduit 20 at a position which is not in line with the light source 10 and the first light sensitive component 14. In the example shown in FIG. 1, the position of the second light sensitive component 18 is generally perpendicular to the line extending between the light source 10 and the first light sensitive component 14, but other angular arrangements are also known by those skilled in the art. Scattered light emanating from the light source 10 and received by the second light sensitive component 18 is represented by arrow S. In some turbidity sensors known to those skilled in the art, the light source 10, the first light sensitive component 14 and the second light sensitive component 18 are disposed within a housing 24 that is arranged around conduit 20. Within the housing 24, the necessary electrical connections between the light source and light sensitive components can be contained.

When light is emitted from the light source 10, as indicated by arrow E, it travels into the fluid 28. If the fluid contains particulates 29, some of the light is scattered, as indicated by arrow S, and some of the light is transmitted to the first light sensitive component 14, as represented by arrow T. By observing the magnitude of light intensity received by the first and second light sensitive components, 14 and 18, the amount of particulates 29 can be determined. To those skilled in the art, the measurement of light passing through the particulates 29 from the light source 10 to the first light sensitive component 14 is referred to as sensing the turbidity of the fluid. The light that is scattered by the particulates 29 and received by the second light sensitive component 18 can also be used as a representation of the amount of particulate matter in the fluid. This measurement of scattered light is sometimes referred by those skilled in the art as nephelometry. For purposes of simplicity, both types of measurements will be referred to herein as turbidity measurements.

As the turbidity of the fluid in the conduit 20 increases, the magnitude of light received by the first light sensitive component will decrease and the magnitude of light received by the second light sensitive component 18 will increase. Therefore, a ratio of the signals received by the first and second light sensitive components can be used as an indicator of the degree of turbidity of the fluid within the conduit 20.

Figure 2:
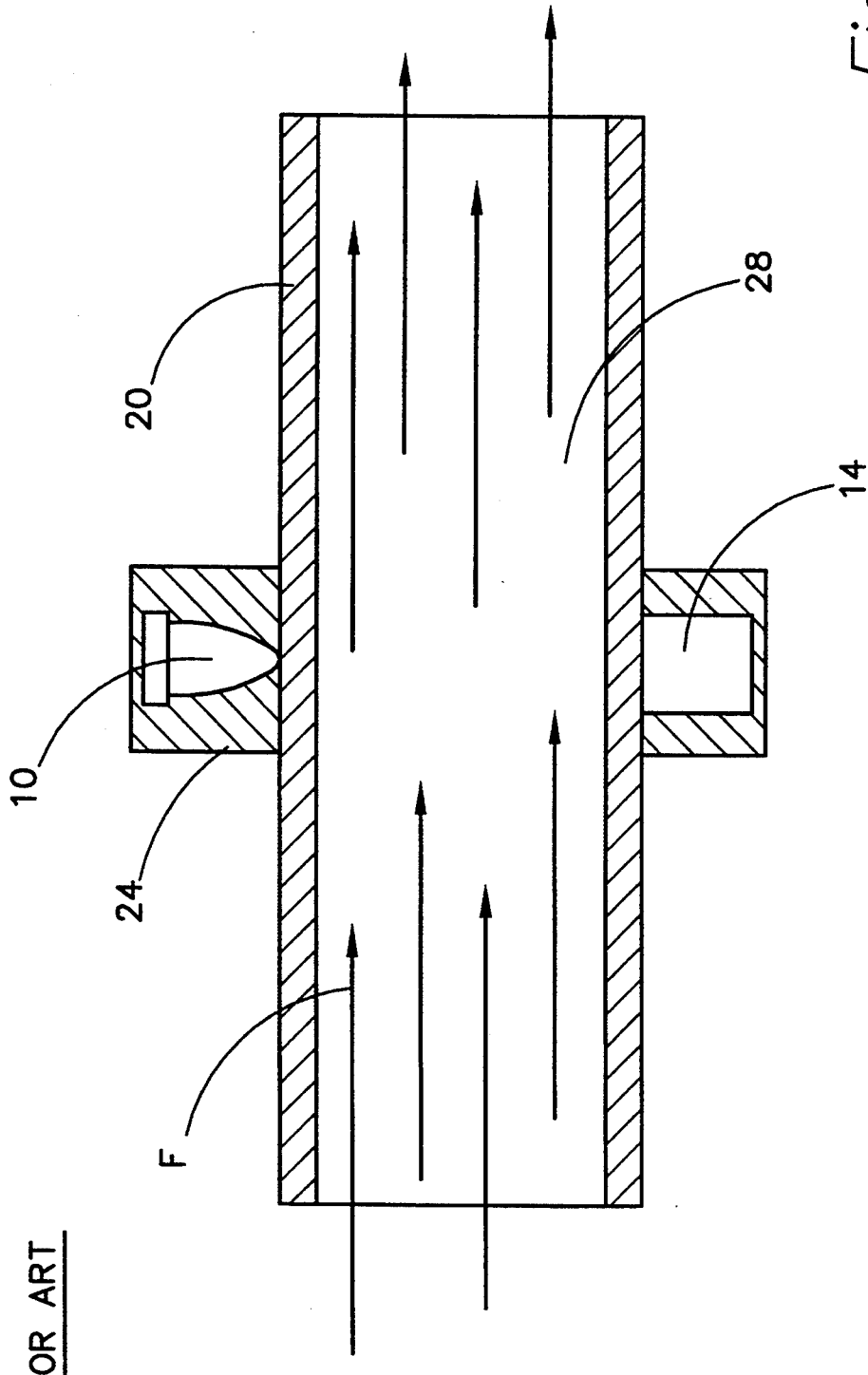
FIG. 2 is a side view of the turbidity sensor shown in FIG. 1.

FIG. 2 illustrates a side sectional view of the device represented in FIG. 1. As can be seen, the conduit 20 provides a means through which a fluid can flow, as represented by arrows F. The housing 24 is disposed around the conduit 20 and provides a compartment within which the light source 10 and first light sensitive component 14 can be disposed. Although not shown in FIG. 2, the second light sensitive component is also disposed within the housing 24. An arrangement such as that shown in FIG. 2 permits the turbidity of the fluid flowing through the conduit 20 to be measured.

With reference to FIGS. 1 and 2, it can be seen that this means for measuring turbidity requires the use of some sort of fluid conducting means, such as the conduit 20, to be used to conduct a fluid through a preselected detection zone. In addition, it can be seen that the incorporation of additional sensors, such as conductivity, temperature and motion detectors, is difficult to achieve in close proximate association with the type of configurations shown.

Figure 3:
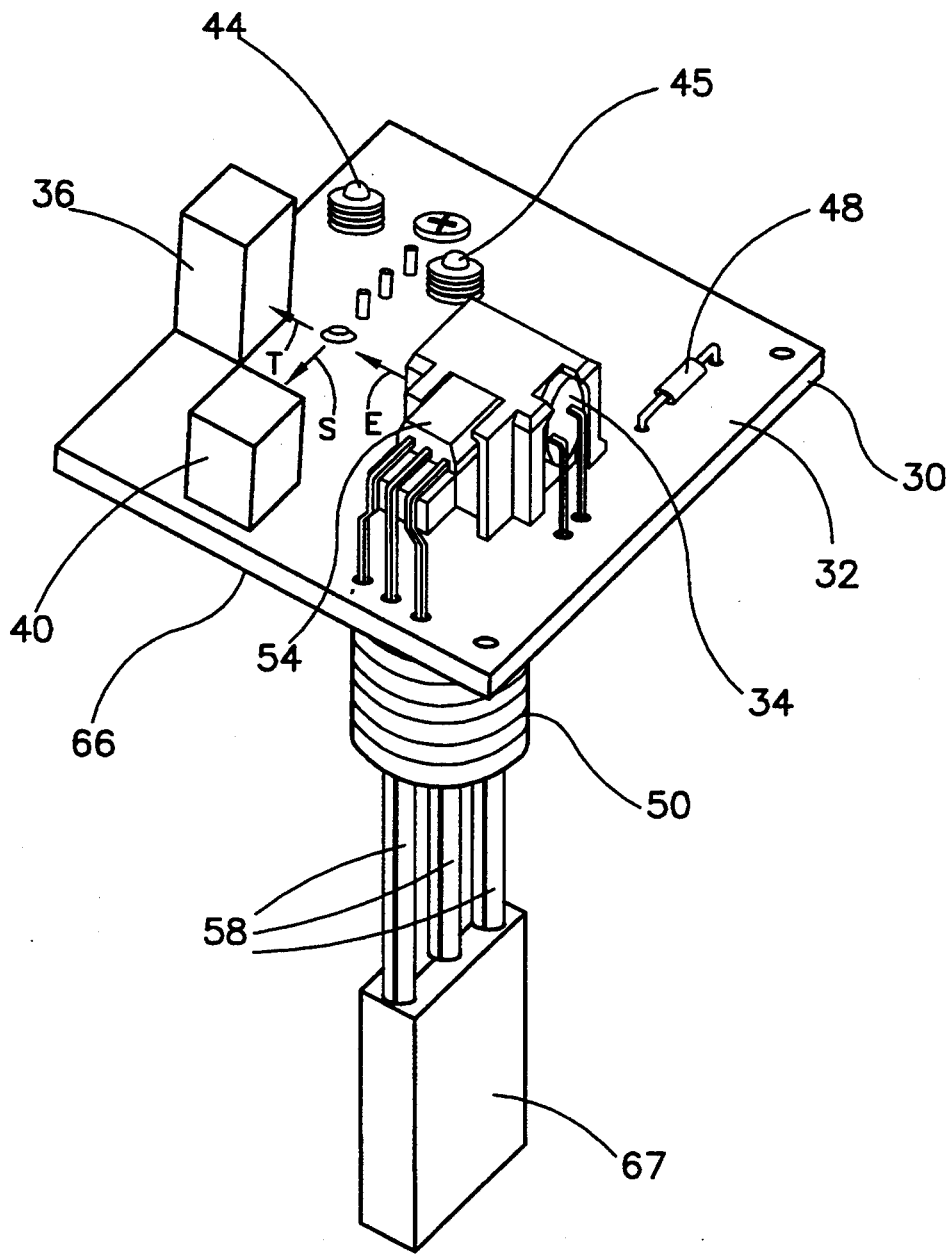
FIG. 3 is a perspective view of the present invention.

FIG. 3 shows a preferred embodiment of the present invention. It comprises a substrate 30 which can be a printed circuit board. Although not shown in FIG. 3 for purposes of clarity, a plurality of conductive runs are disposed on the first surface 32 of the substrate 30. A light source 34, which can be a light emitting diode, is attached to the first surface 32 of the substrate 30 the light source 34 is arranged in association with the substrate 30 to direct a beam of emitted light E in a direction generally parallel to the first surface 32. A first light sensitive component 36, which can be a photodiode, is also attached to the first surface 32 of the substrate 30 and disposed at a position to receive transmitted light T that is emitted from the light source 34 and travels in a direction parallel to the first surface 32 and travels toward the first light sensitive component 36. A second light sensitive component 40 is also attached to the first surface 32 of the substrate 30 and is positioned at a location to receive scattered light S emitted from the light source 34. Although not shown in FIG. 3, it should be understood that the scattered light S results from the emitted light E impinging against and being deflected by a plurality of particulates in the region between the light source 34 and the first light sensitive component 36. As can be seen in FIG. 3, the present invention utilizes no conduit to direct fluid between the light source and the first light sensitive component. In addition, it utilizes no reservoir, or well, to contain the fluid. In a manner that is generally known to those skilled in the art, signals provided by the first light sensitive component 36 and the second light sensitive component 40 can be used in association with each other to determine a value of the turbidity of a fluid in a detection zone proximate the first surface 32 of the substrate 30 and between the light source 34 and the first light sensitive component 36.

The present invention also provides two conductors, 44 and 45, which are displaced from each other by a preselected distance. The two conductors, 44 and 45, are maintained at a preselected voltage potential relative to each other. The voltage potential, in a preferred embodiment of the present invention, is an alternating voltage and means are provided for preventing a DC offset voltage from being maintained on either of the two conductors. When a fluid is disposed between the two conductors, the conductivity of the fluid can be determined through appropriate circuitry that is known to those skilled in the art. This conductivity measurement can be used to determine the types of solids suspended in the fluid proximate the first surface 32 of the substrate 30. Although the conductivity measurement can be used for many purposes, it is particularly advantageous for determining whether or not dishwasher detergent is dissolved in the fluid proximate the substrate.

A temperature measuring means 48 is also attached to the first surface 32 of the substrate 30. Its purpose is to permit the measurement of the fluid temperature proximate the first surface 32. In order to provide for increased efficiency in the operation of a dishwasher of other appliance for washing articles, the temperature of the fluid used in the cleansing process can provide useful information in monitoring and controlling the operation of the appliance.

In a particularly preferred embodiment of the present invention, a magnetically sensitive component 54 is also attached to the substrate 30. In one embodiment of the present invention, the magnetically sensitive component 54 is disposed proximate and attached to the light source 34. However, it should clearly be understood that the magnetically sensitive component 54 can be disposed at alternative locations on the substrate 30. In a most preferred embodiment of the present invention, the magnetically sensitive component comprises a magnetoresistive element to detect the presence of a ferromagnetic component proximate the magnetically sensitive component 54. When the present invention is employed in conjunction with a dishwasher, the magnetically sensitive component can detect the presence of a magnet or a ferromagnetic component attached to the washer arm. As the washer arm rotates about its central axis, the magnetically sensitive component 54 can detect the passage of the arm component as it rotates. This permits a microprocessor to determine the speed of rotation of the arm and, in addition, can permit the microprocessor to determine whether or not the arm is rotating at a satisfactory speed. Extending from a second surface 66 of the substrate 30, is a housing 50 that is shaped to contain a plurality of conductors therein. The housing 50 is attached to the second surface 66 and the conductors are connected in electrical communication with the conductive runs on the first surface 32 which permit electrical communication between the light source 34, the first light sensitive component 36, the second light sensitive component 40, the two conductors, 44 and 45, the temperature sensitive component 48 and the magnetically sensitive component 54. Although the temperature sensitive component 48 can be a thermistor, other elements can be used to perform this function of measuring the temperature of the fluid proximate the first surface 32. Reference numeral 58 represents a conductor extending from the housing 50. Connector 67 facilitates assembly of the device and connection between it and other control components.

With continued reference to FIG. 3, it should be understood that all of the components shown on the first surface 32 are rigidly attached to the substrate 30 and form a unitary structure with the substrate.

Figure 4:
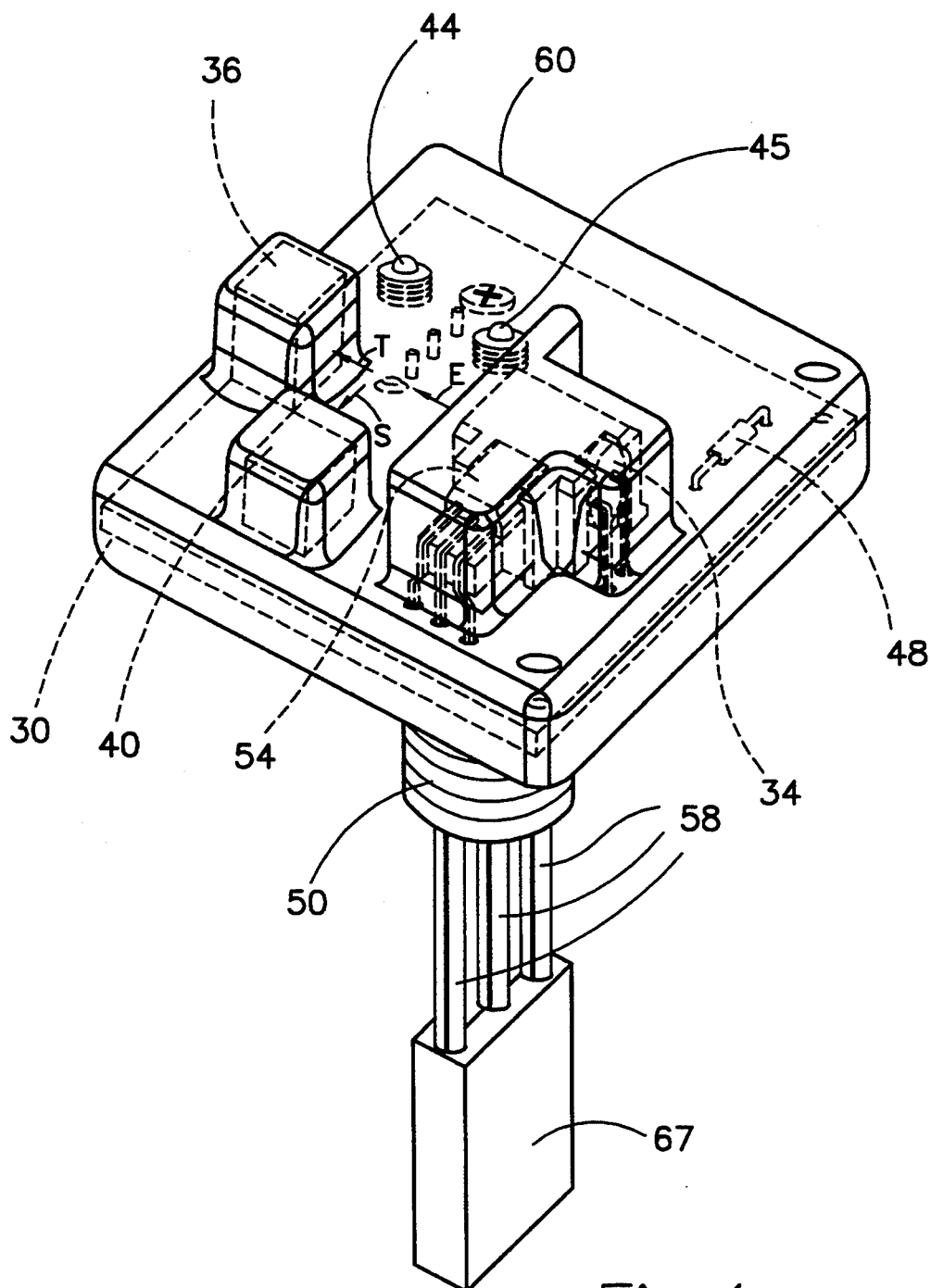
FIG. 4 is a view of the sensor cluster of FIG. 3 with a coating of light transmissive and liquid impermeable material.

FIG. 4 shows the device of FIG. 3 after it is overmolded with a light transmissive and fluid impermeable coating of clear epoxy. The substrate 30 and all of it's attached components are contained within the encapsulating material 60. The two conductors, 44 and 45, extend through the overmolded material so that they can be disposed in electrical communication with the fluid proximate the first surface 32 in order for them to perform their function of measuring the conductivity of the fluid.

With reference to FIGS. 3 and 4, the housing 50 can be threaded on its outer surface to permit it to be attached in threaded association with a surface of some device in which it is to be located. In some embodiments of the present invention, the housing 50 need not be threaded, Instead, it can be provided with a slightly compressible material that permits it to be inserted into an opening in such a way that it maintains a fluid tight attachment between its outer surface and the opening.

Figure 5:
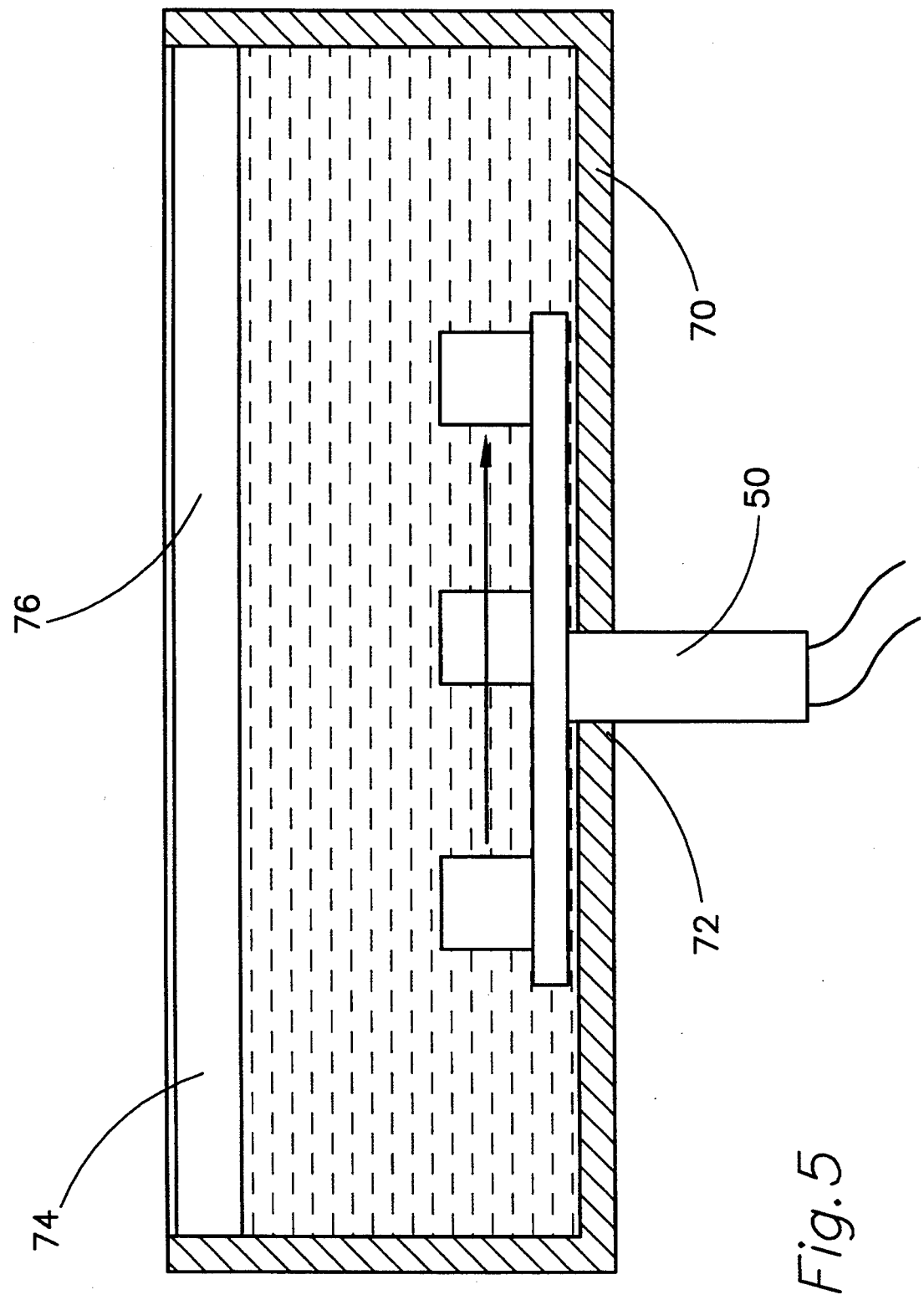
FIG. 5 is a schematic illustration of one application of the present invention.

FIG. 5 schematically illustrates one advantageous way in which the present invention can be used. If it is desirable to measure the turbidity of a fluid in a tank 70, the housing 50 can be inserted through a hole 72 formed in the bottom of the tank 70. This permits the sensor cluster shown in FIG. 4 to be located proximate the bottom portion of the tank. Since the light source and the first and second light sensitive components are disposed below the surface of the fluid 74, the fluid is within the detection zone between the light source and the first light sensitive component and its characteristics can be measured. In other words, the turbidity of the fluid 74, the conductivity of the fluid 74 and the temperature of the fluid 74 can be determined by the instruments of the sensor cluster. As long as the ullage 76 is above the operative portions of the sensor components on the substrate, these characteristics can be monitored and used to control an appliance, such as a dishwasher.

Figure 6:
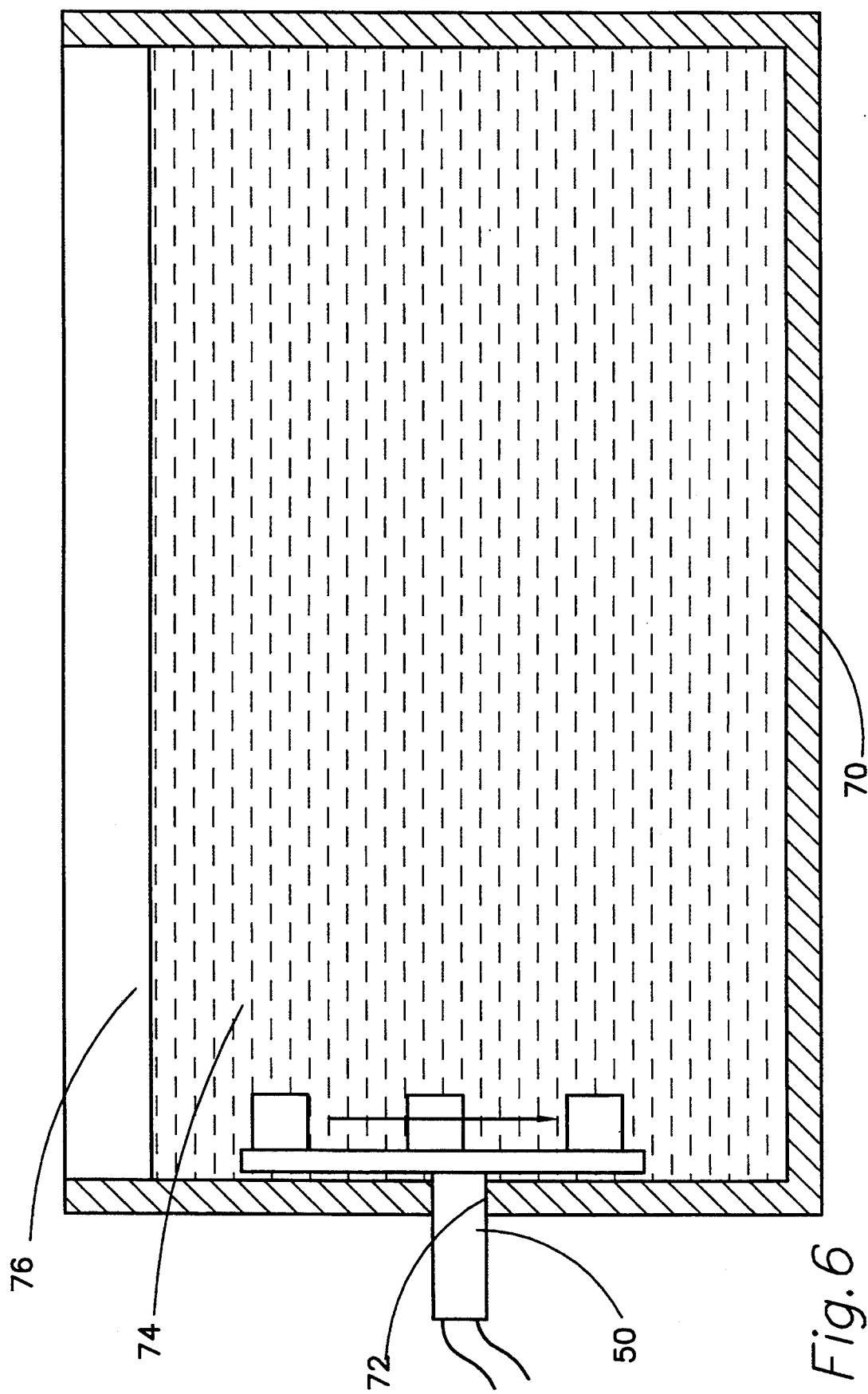
FIG. 6 is a schematic illustration of another application of the present invention.

FIG. 6 schematically shows an alternative configuration in which the sensor cluster of the present invention in mounted on a side wall of a tank 70. The housing 50 is inserted through a hole 72 and sealed to prevent leakage of the fluid 74. As long as the sensors which are attached to the first surface of the substrate 30 are disposed below the surface of the liquid 74 and below the ullage 76, the sensors of the cluster can provide information regarding the turbidity, the conductivity and the temperature of the fluid 74.

FIGS. 5 and 6 illustrate one advantage of the present invention. It can be used in virtually any position and in virtually any type of device in which a liquid is present as long as the light sensitive components are not adversely affected by ambient light from external sources. It does not require any conduit or tubing to direct the fluid past a predetermined location in order for the present invention to measure the turbidity, conductivity and temperature of the fluid. In addition, it does not require a reservoir or well to be located at a particular place relative to the first surface of the substrate. Instead, the sensor cluster can be located at any advantageous position as long as its sensor components are disposed below the surface of the liquid.

Figure 7:
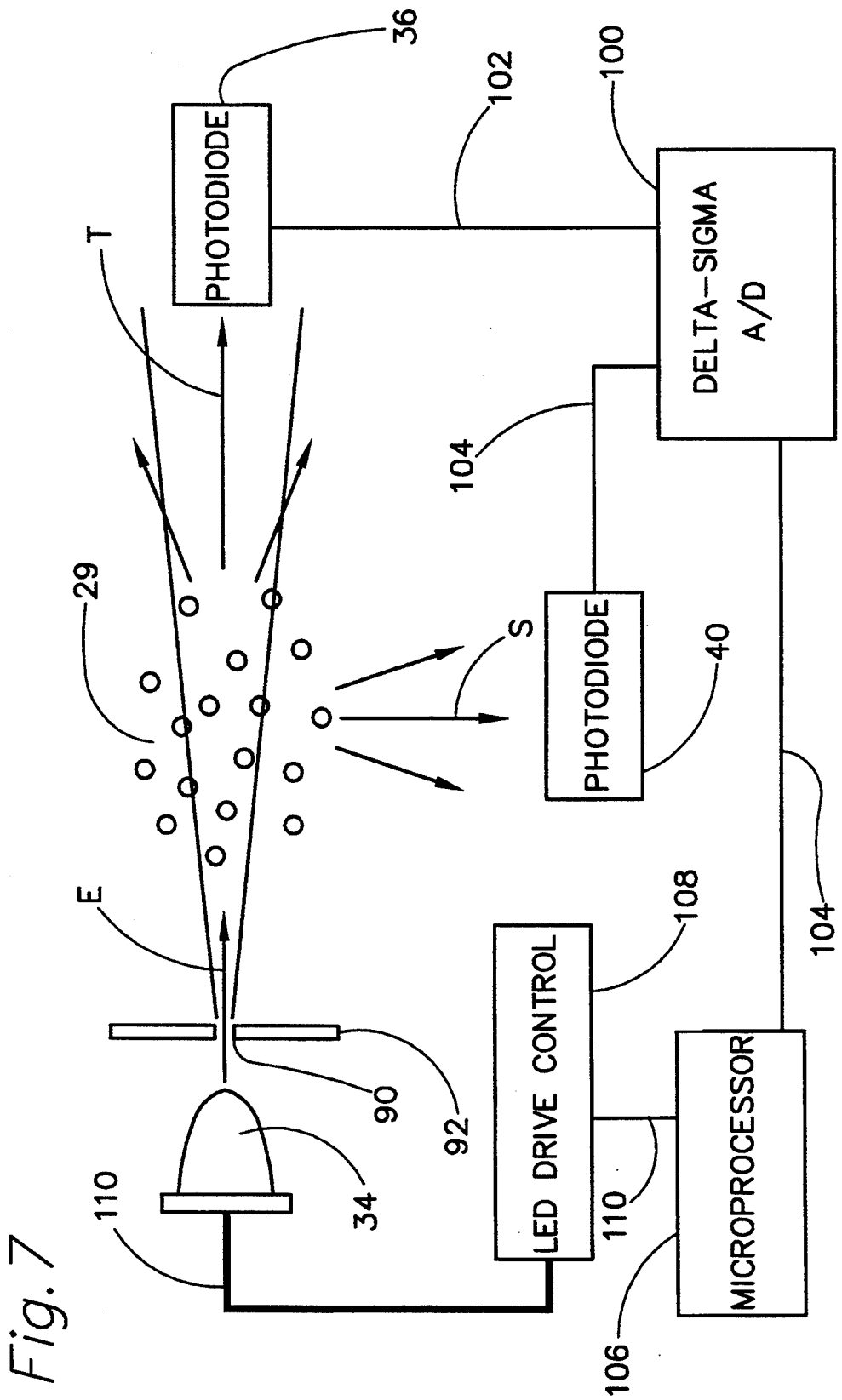
FIG. 7 is a schematic block diagram of a circuit used to monitor and control a turbidity sensor.

FIG. 7 illustrates a schematic diagram that shows a means by which the turbidity detector of the present invention can be operated. As described above, the light source 34 provides a beam of emitted light E which passes through the particulates 29 of a fluid. The transmitted light beam T is sensed by a first light sensitive component 36, such as photodiode, and the scattered beam S is sensed by a second light sensitive component 40, which can also be a photodiode. In a particularly preferred embodiment of the present invention, the emitted light E is directed through an opening 90 formed in a surface 92. The purpose of the opening 90 is to define a preselected area of the first light sensitive component 36 on which the light will be shown. In a manner which is generally known to those skilled in the art, a delta-sigma analog-to-digital conversion technique can be used. This technique is described in considerable detail in patent application serial no. 08/053,042 (T10-14718) which was filed on Apr. 6, 1993 by Kubisiak et. al. and is assigned to the assignee of the present application. This patent application is explicitly incorporated by reference herein. The deltasigma A/D 100 is connected to the first and second light sensitive components, 36 and 40, by lines 102 and 104, respectively. After the signals from the first and second light sensitive components are combined, a signal is provided on line 104 to microprocessor 106. The signal on line 104 permits the microprocessor 106 to determine the turbidity of the fluid. In addition, as will be described in greater detail below, it also permits the microprocessor 106 to control the current provided to the light source 34, which in a preferred embodiment of the present invention is a light emitting diode. The LED drive control 108 is used to provide a variable magnitude of electrical current, on line 110, to the light diode which serves as the light source 34. The circuitry used to regulate the current provided to the light source will be described in greater detail below. However, it should be understood that the circuitry is used to regulate the current to the light source as a function of the signals received from the first and second light sources, either taken individually or together.

Figure 8:
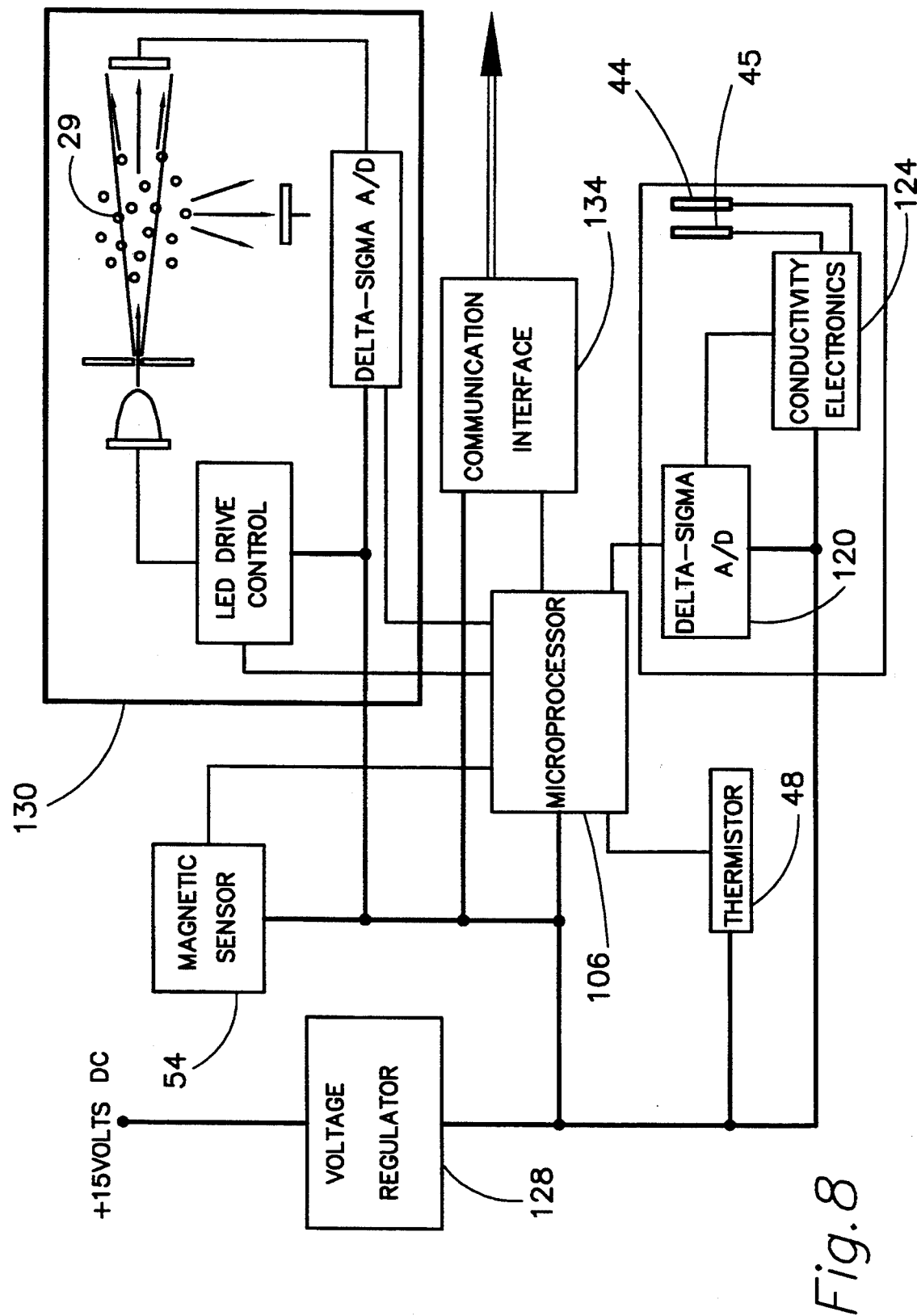
FIG. 8 is a schematic diagram of a circuit used in conjunction with the present invention.

FIG. 8 is a schematic diagram of the circuitry used to monitor the turbidity, the temperature, the magnetic sensor 54 and the conductivity of the fluid proximate the first surface of the substrate of the sensor cluster. Although many other alternative circuits can be used in conjunction with the present invention, the diagram in FIG. 8 represents one possible way of monitoring these fluid characteristics. In addition, it incorporates a means by which the magnetic sensor, or magnetically sensitive component, can be monitored.

In FIG. 8, the microprocessor 106 is connected in signal communication with the LED drive control 108 and the delta-sigma A/D 100 as described above. In addition, it is connected in signal communication with a delta-sigma A/D 120 that is associated with conductivity electronics 124 for monitoring the conductivity between the conductors, 44 and 45, which have been described above.

The microprocessor 106 is also connected in signal communication with a temperature sensor 48, which can be a thermistor. A voltage regulator 128 provides regulated power to the microprocessor 106, the thermistor 48, the conductivity sensing components, the magnetic sensor 54 and the components related to the measurement of turbidity which are identified by reference numeral 130 in FIG. 8. The magnetically sensitive component 54, which is a magnetoresistive array in a preferred embodiment of the present invention, is also connected in signal communication with the microprocessor 106.

With continued reference to FIG. 8, a communication interface 134 is provided so that the microprocessor can communicate with external components of the dishwasher or similar appliance. The signals provided by the communication interface 134 permit other control circuitry of the appliance to react to the measurements of turbidity, temperature and conductivity and also permit other control components to react to the results of the magnetic sensor measurements described above.

As described above, in conjunction with FIGS. 3-8, the present invention provides a singular structure that is a sensor cluster which can be associated with many different types of fluid monitoring applications. The single structure of the sensor cluster permits the measurement of turbidity, conductivity and temperature and also allows the sensor cluster to be disposed proximate the path of a moving ferromagnetic object in order to permit the cluster to monitor movement of the ferromagnetic object, such as a spray arm of a dishwasher. By disposing the plurality of sensors in a single unitary cluster, the present invention provides a device which can easily accommodate many different requirements of a fluid condition sensor. It also removes the necessity of mounting a plurality of sensor to various portions of an appliance and connecting those individual sensors together in signal communication as would be required if the individual sensors were not combined in an advantageous cluster as described above.

Figure 9:
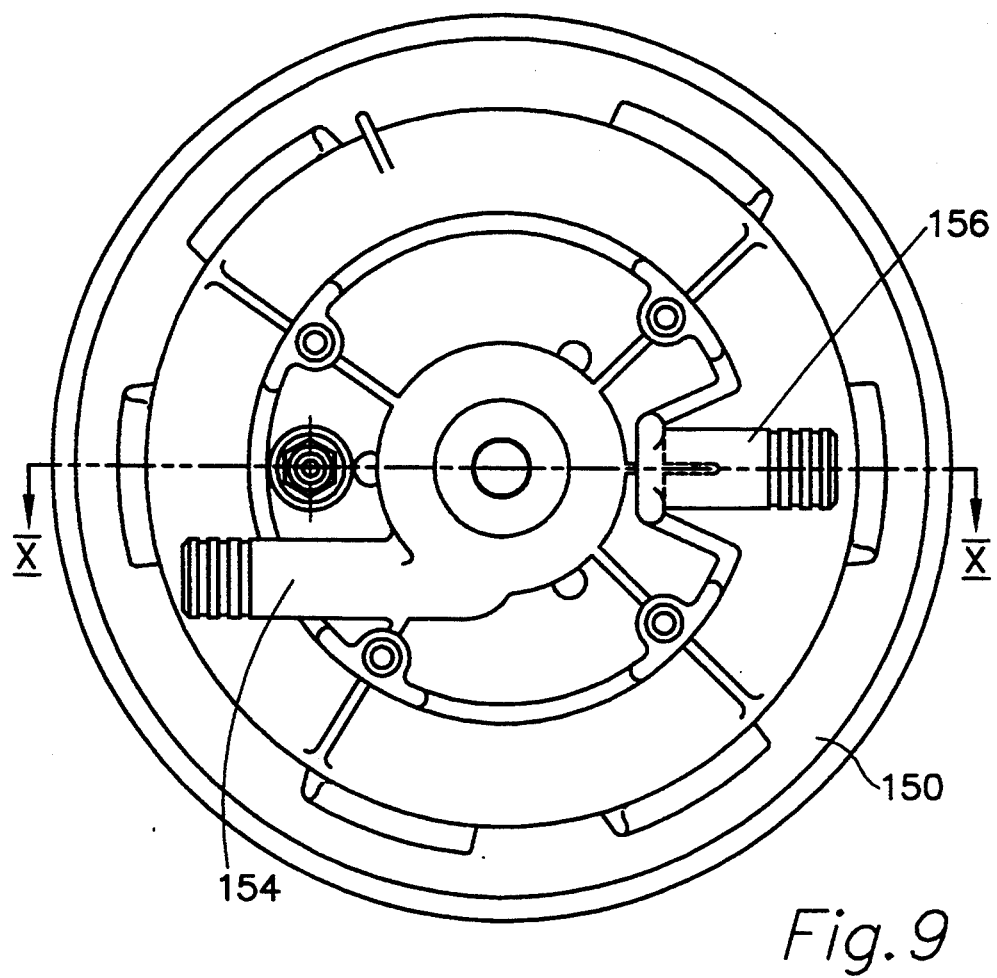
FIG. 9 is a bottom view of a lower pump housing used in a dishwasher.

As described above, the present invention provides a sensor cluster for use in association with various types of mechanisms which require the ability to determine the turbidity and other characteristics of a fluid. For example, the present invention enables an appliance, such as a dishwasher to monitor the turbidity of its washing fluid without requiring the use of conduits, tubings, reservoirs or wells particularly adapted for the turbidity sensor. FIG. 9 shows a bottom view of a lower pump housing 150 which can be used in a dishwasher appliance. In FIG. 9, it can be seen that the housing is provided with an inlet/outlet conduit 154 and an upper wash arm supply conduit 156 through which liquid passes during various portions of the normal dishwashing cycle.

Figure 10:
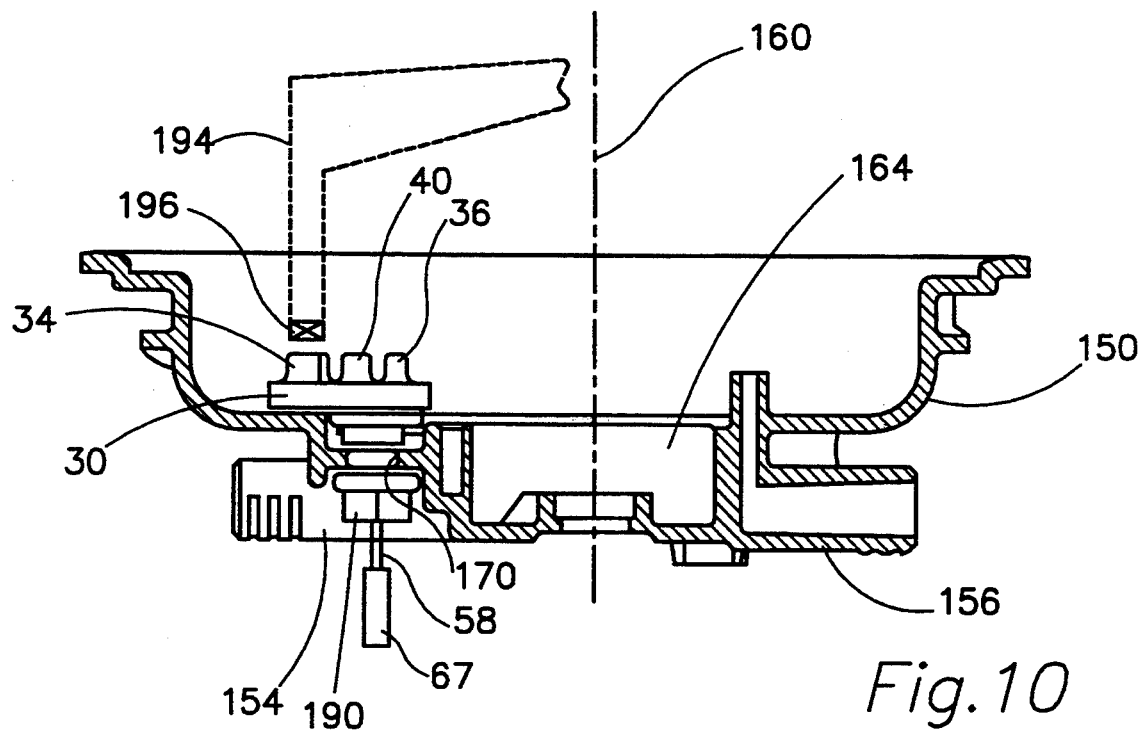
FIG. 10 is a sectional view of the illustration shown in FIG. 9.

FIG. 10 shows a sectional view of the lower pump housing 150 of FIG. 9. Although not shown in FIG. 10, it should be understood that a motor would typically be mounted directly under the lower pump housing 150 in line with the centerline 160 and, in addition, that a rotatable pump assembly would be mounted in the cavity 164 formed in the lower pump housing 150. To simplify the illustration, the motor and the rotatable pump assembly are not shown in FIG. 10. A hole 170 is formed in the lower pump housing and the housing 50 of the sensor cluster is inserted through the hole 170. As shown in FIG. 10, the housing 50 extends downward through the hole 170 and the conductors 58 and connector 67 are disposed below lower pump housing for connection to another cable of the appliance. Extending above the bottom surface of the lower pump housing, the substrate 30 supports the light source 34, the first light sensitive component 36 and the second light sensitive component 40. Although not shown in FIG. 10, it should be understood that the substrate 30 would also support the temperature sensitive device 48 and the two conductors, 44 and 45, that provide the conductivity sensing elements. In addition, the magnetically sensitive component 54 is disposed within the same pedestal in which the light source 34 is contained. A nut 190 is operatively associated in threaded association with the housing 50 in order to rigidly attach the sensor cluster to the lower pump housing 150.

With continued reference to FIG. 10, a washer arm 194 is schematically illustrated by dashed lines. Although FIG. 10 only shows a partial segment of the washer arm 194, it should be understood that the washer arm is generally symmetrical about centerline 160. The washer arm 194 rotates about centerline 160 to direct a spray of water in a predetermined pattern. The magnetically sensitive component 54 that is contained within the sensor cluster of the present invention is operatively positioned to detect a permanent magnet 196 that is attached to the washer arm 194. In this way, the magnetically sensitive component can detect movement of the magnet through a detection zone proximate the sensor and determine the passage of the washer arm past the sensor cluster. Using this technique, control electronics can determine that the washer arm 194 is moving and, in addition, can determine the speed of movement by counting the signal pulses received when the magnet 196 passes over the magnetically sensitive component during a preselected period of time.

By eliminating the requirement for a fluid conduit or a reservoir particularly adapted for use by the turbidity sensor, the present invention enables the turbidity sensor and its associated components to be advantageously located in a region within the lower pump housing 150 where the movement of the washer arm 194 can easily be monitored. This adaptability would not other wise be possible if the turbidity sensor was required to be incorporated in association with a clear conduit, or tube, as is known in the prior art. In addition, this adaptability would also be severely limited if the turbidity sensor required the use of a specifically provided reservoir as is taught in the prior art.

In turbidity sensors, whether they use a single light sensor or two light sensors as described above, are susceptible to variations in their light intensity measurements because of the possibility that the light source may vary in intensity. This is particularly true if the light source is a light emitting diode. It is possible that the light intensity emitted by a light emitting diode, for any given current passing through the diode, can vary by as much as a factor of three. In addition, light emitting diodes are subject to aging which decreases the light intensity for any particular current flowing through the diode. Although the methodology described above, wherein a ratio of two light sensors is taken, reduces the vulnerability of the turbidity sensor to changes in light intensity, turbidity sensors of this type are subject to saturation of one or both of the light sensors. A turbidity sensor made in accordance with the present invention minimizes this vulnerability by regulating the current through the light emitting diode as a function of the signals received by the light sensors.

Figure 11:
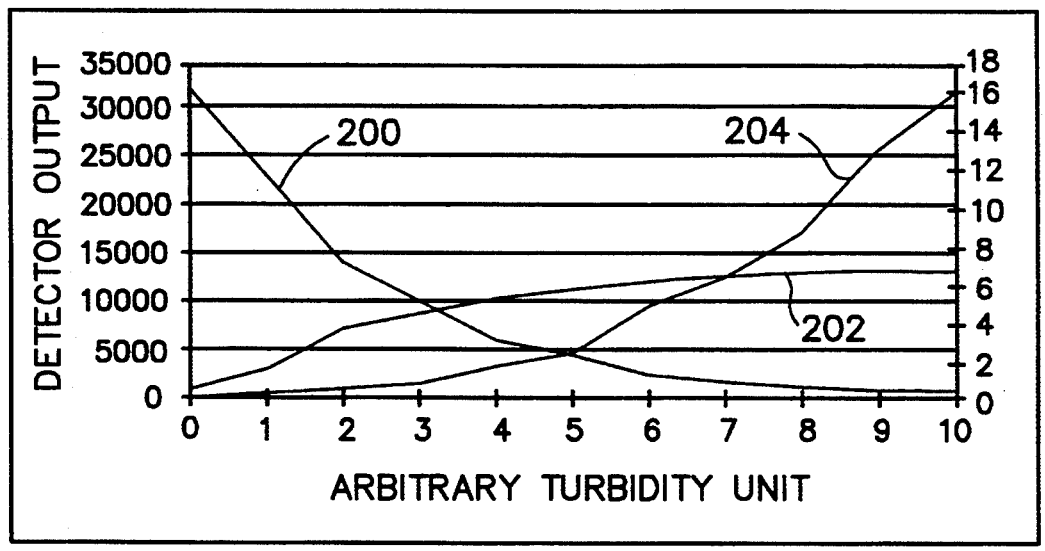
FIG. 11 is a graphical illustration used to represent the operation of a turbidity sensor.
Figure 12:
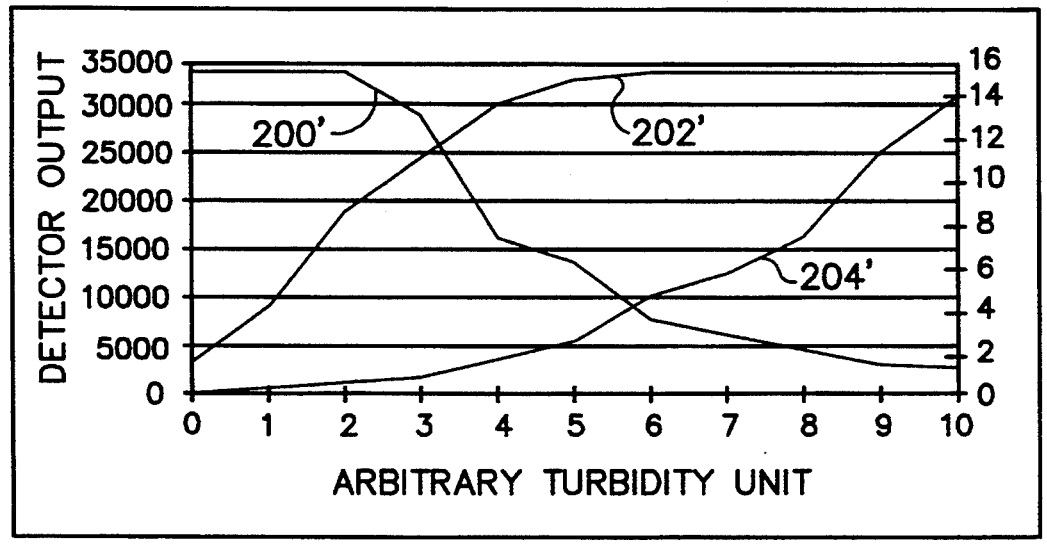
FIG. 12 is a graphical representation of the signals of a turbidity sensor under certain disadvantageous conditions.

To illustrate this problem, FIGS. 11 and 12 represent the signals provided by the first and second light sensors of a turbidity sensor and the ratio of those signals. In FIGS. 11 and 12, the detector outputs are represented as a function of arbitrary turbidity units. Although arbitrary, a turbidity value of 10 represents extremely turbid liquid and a turbidity value of zero represents virtually clear liquid. In FIG. 11, curve 200 represents the signal provided by a light sensitive component disposed to receive light transmitted directly through a liquid from a light emitting diode. As can be seen, in a clear liquid the detector output is at its maximum value and, as turbidity increases, the magnitude of the first signal from the first light sensitive component decreases. FIG. 11 also shows curve 202 which represents the second output from the second light sensitive component that is disposed to receive scattered light which is dispersed and reflected by particulate matter 29 in the liquid. Curve 204 represents the ratio of the scattered light 202 and the transmitted light 200. The ratio of the scattered and transmitted light signals from the first and second light sensitive components can be used as an indicator of the turbidity of the fluid passing through the detection zone. If, hypothetically, the light emitting diode emits a light of an intensity greater than that used to generate the curves in FIG. 11, curves 200 and 202 would both increase proportionally but the ratio 204 should remain approximately the same as indicated. This ratio technique avoids the problems described above that could be caused by changes in the intensity of light emitted by the light emitting diode. However, if the light emitting diode emits light that is sufficient to saturate the components used to amplify the signals from the light sensitive components, either curve 200 or curve 202 could be distorted. It should be understood that the amplification techniques used for the first and second light sensitive components could cause either of the two signals to saturate before the other. For purposes of this discussion, the maximum values of curve 200 are greater than the maximum values of curve 202 and, therefore, curve 200 would be more likely to saturate if the intensity of light emitted by the light emitting diode increases beyond the level necessary to result in this saturation.

FIG. 12 illustrates a hypothetical example wherein the intensity of light emitted by the light emitting diode of the turbidity sensor is sufficient to increase the magnitudes of both curves 200 and 202 to levels which result in saturation of the components used to amplify those signals. In FIG. 12, curve 200' represents curve 200 increased to a magnitude that results in saturation and, similarly, curve 202' represents curve 202 increased to a magnitude sufficient to result in saturation. For purposes of this exemplary discussion, the arbitrary value of 34,000 is used as the saturation level for both curves 200' and 202'. This can be seen in the illustration of FIG. 12. Because of the saturation of these two signals, the resulting ratio represented by line 204' is incorrect where either of the two curves from the light sensitive components is saturated, particularly for low turbidity values when curve 200' is saturated.

With continued reference to FIGS. 11 and 12, it would be significantly advantageous if the light intensity emitted by the light emitting diode could be regulated to avoid saturation of one or both of the signals provided by the first and second light sensitive components.

Figure 13A:
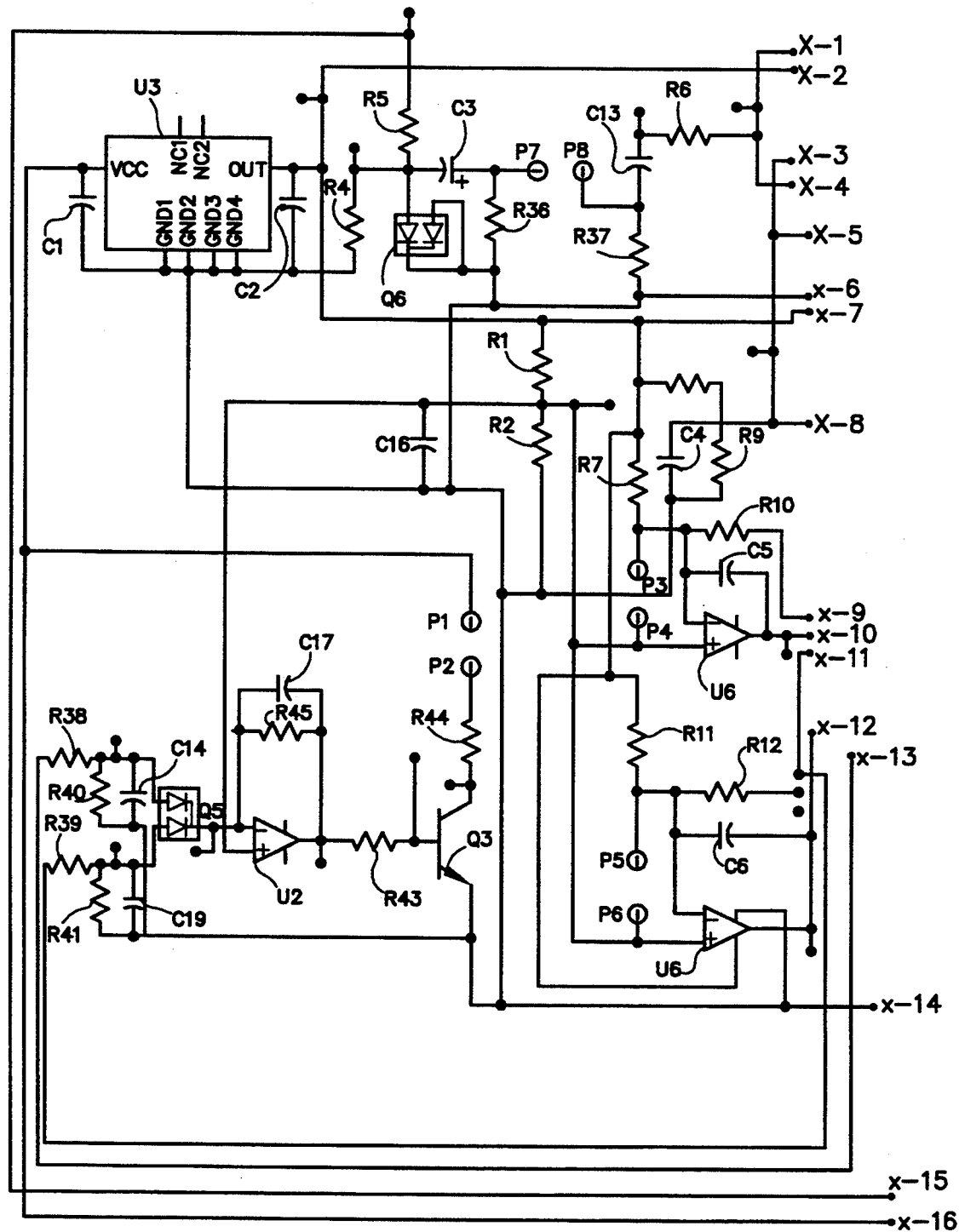
FIGS. 13A, 13B and 13C are portions of a schematic circuit can be used in association with the present invention.
Figure 13B:
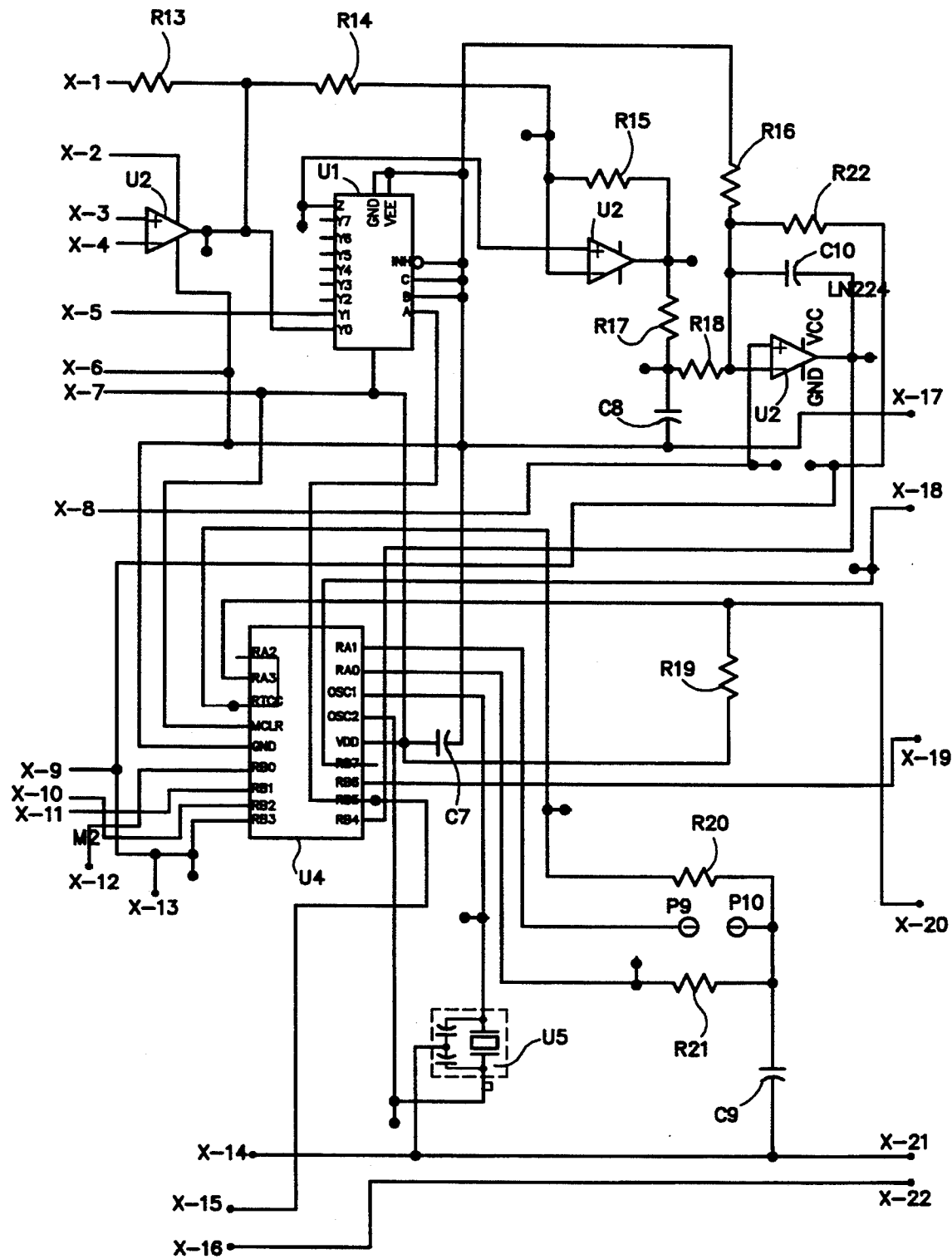
Figure 13C:
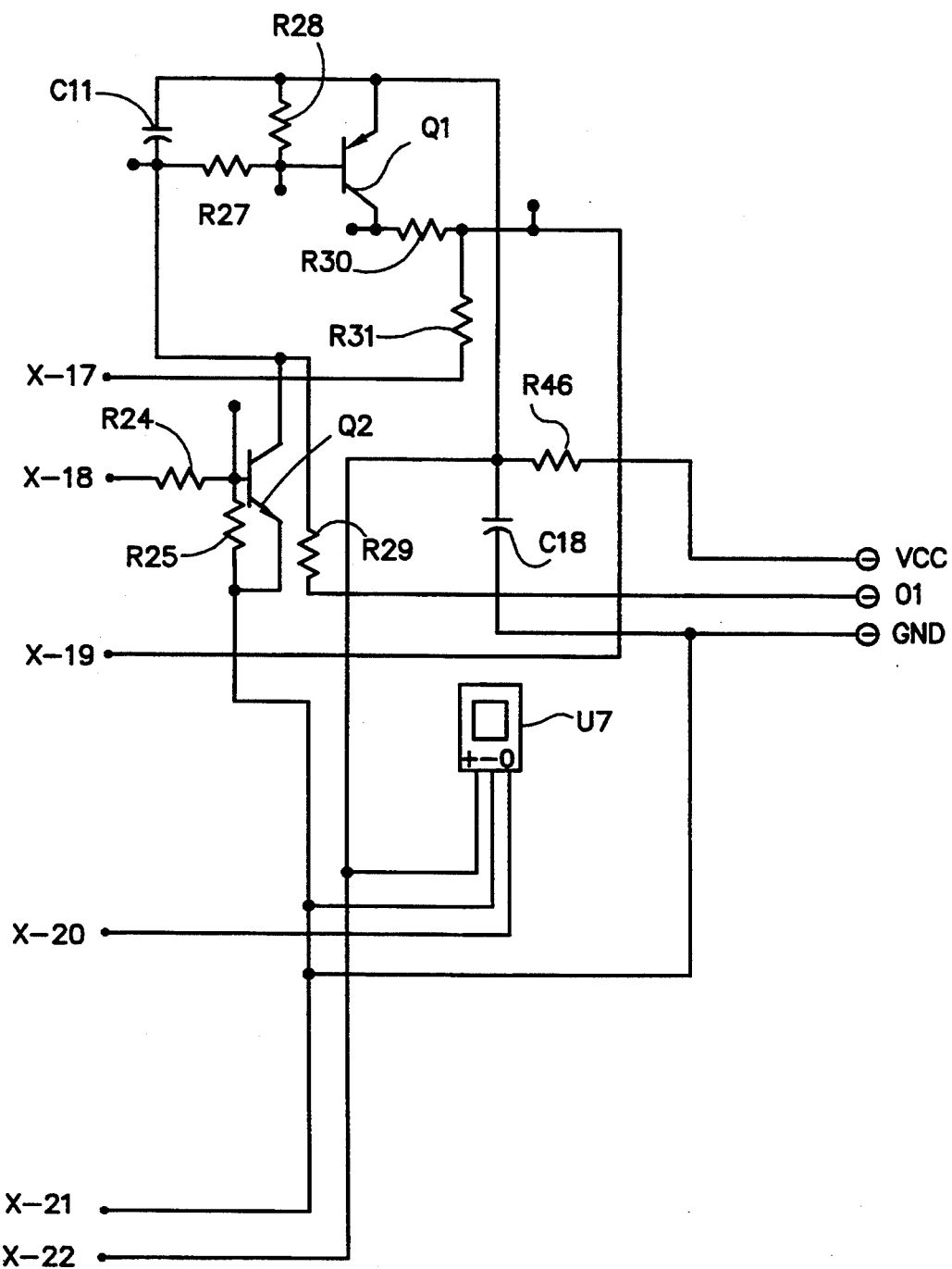

FIG. 13 shows a circuit used in a preferred embodiment of the present invention. Resistor R12 and capacitor C6 are used to integrate the pulses from the RB1 output of microprocessor U4 and this integrated signal is connected to the inverting input of operational amplifier U6. This same signal is provided to the low pass filter which comprises resistor R39 and capacitor C19. It should be understood that the signal provided by the RB1 output of microprocessor U4 is digital as is normal when the sigmadelta technique is used. This technique is well known to those skilled in the art and is described above. The low pass filter which comprises resistor R39 and capacitor C19 provides a DC input at the anode of the diode pair Q5. In a manner similar to that described immediately above, the RB3 output of microprocessor U4 provides a signal which is integrated by resistor R10 and capacitor C5 and connected to the inverting input of operational amplifier U6.

In a preferred embodiment of the present invention, a photodiode is connected across points P3 and P4 and another photodiode is connected across points P5 and P6. The first photodiode connected across points P3 and P4 is the light sensitive component used to receive light transmitted directly through the fluid from the light emitting diode. The photodiode connected across points P5 and P6 is the light sensitive component used to detect scattered light. Also in a preferred embodiment of the present invention, the light emitting diode is connected across points P1 and P2 in FIG. 13.

With continued reference to FIG. 13, the pair of diodes contained in Q5 selects the higher of the two signals received from low pass filters which comprise resistor R39 and capacitor C19 and resistor R12 and capacitor C6, respectively. The maximum value of those two signals is connected to the inverting input of operational amplifier U2. The output of operational amplifier U2 is connected to the base of transistor Q3 and regulates the current passing through the light emitting diode and resistor R44. The noninverting input of operational amplifier U2 is connected to a reference voltage which, in one particular embodiment of the present invention, is 3.5 volts. The voltage provided to the noninverting input of operational amplifier U2 is selected to represent the saturation level, scaled by the voltage dividers, 38, 39, 40 and 41, of the operational amplifiers associated with the first and second light sensitive components. The output of operational amplifier U2 therefor determines if either of the two operational amplifiers associated with the light sensitive components is nearing its saturation level. This output therefore determines the level of current passing through transistor Q3 by regulating its base current. If the magnitude of the signal at the inverting input of operational amplifier U2 approaches the reference voltage at its noninverting input, the base current is decreased and the current through the light emitting diode, at points P1 and P2, is reduced. Therefore, the current passing through the light emitting diode of the turbidity sensor is regulated as a function of the amplified signals from the first and second light sensitive components in order to prevent saturation. It can be seen that operational amplifier U2 also serves another useful purpose. If the amplified signals received from the first and second light sensitive components are extremely low, the output of operational amplifier U2 will be increased and the current flowing through the light emitting diode will also be increased by the action of transistor Q3. Therefore, if the liquid being sensed by the turbidity sensor is extremely turbid and both light sensitive components are receiving severely reduced intensity of light, the brightness of the light emitting diode can be increased to partially overcome this situation.

The action of the operational amplifier U2 therefore serves to maintain the intensity of the light emitted by the light emitting diode at the highest possible level without saturating either of the two amplified signals received from the light sensitive components. This control of the light emitting diode as a function of the signals received from the first and second light sensitive components is made possible because of the fact that the two signals from the light sensitive components are compared as a ratio. If the two signals from the light sensitive components are not compared as a ratio, a technique of this type would not be possible because the effect on the light intensity would adversely affect the ability of the turbidity sensor to accurately measure the turbidity of the liquid.

As discussed above, the signal from either of the two light sensitive components could be saturated while the other is not. Depending on the gain of the amplifiers associated with the first and second light sensitive components, one or both of the amplified signals could be in saturation while the other is not. Although a preferred embodiment of the present invention uses both the first and second signals from the first and second light sensitive components and compares the maximum of those two signals to the reference voltage at the noninverting input of the operational amplifier, either one of the signals alone could be used in this manner. If, for example, the amplification gain of the second scattered signal is much higher than that of the first transmitted signal, it may not be necessary to monitor the transmitted signal in applications where it is not expected to saturate under any condition. On the other hand, if it is anticipated that the transmitted signal will reach magnitudes significantly higher than that of the scattered signal, only the transmitted signal could be used for these purposes. However, it has been found that a preferable circuit arrangement in a preferred embodiment of the present invention uses both signals from the first and second light sensitive components and selects the maximum of those two signals for use in controlling the current through the light emitting diode at points P1 and P2.

With continued reference to FIG. 13, the pins, P7 and P8, serve to connect the conductors, 44 and 45, to the circuit shown in FIG. 13. The microprocessor U4 provides a series of pulses from its RB5 output. In a preferred embodiment of the present invention, the pulses are a 20KHz squarewave with a 50 percent duty cycle and an amplitude that ranges from zero to five volts. Those pulses are provided to resistor R5 which is connected to ground through the diode Q6 as shown. This provides a voltage level at the anode of the diode Q6 that varies from 0 to 0.6 volts. Through the action of capacitor C3, the signal at pin P7 varies from plus 0.3 volts AC to minus 0.3 volts AC. The inverting input of inverting amplifier U2 is connected, through resistor R6 and capacitor C13, to pin PS. The gain of inverting amplifier U2 is equal to the resistance of resistor R13 divided by the sum of the resistances of resistor R6 and the impedance of the solution between points P7 and PS. The output of the inverting amplifier U2 is connected to the Y0 input of analog multiplexer U1. The A input of analog multiplexer U1 is connected to the source of the 20KHz pulses. As a result, the Z output of the analog multiplexer U1 alternates between the output signal from the inverting amplifier U2 and the signal provided to the noninverting input of the inverting amplifier U2. Output Z from the analog multiplexer is connected to the noninverting input of the amplifier U2 whose inverting input is connected to the signal provided through resistor R14. The amplifier U2 whose output is connected between resistor R15 and resistor R17 provides a quasi-DC signal which is the result of the alternating action of the analog multiplexer and the operation of amplifier U2. During the negative half cycles of the output of inverting amplifier U2, which are provided as the Y0 input of analog multiplexer U1, the U2 amplifier acts as a unity gain inverting amplifier and, during the positive half cycles of the output of the inverting amplifier U2 acts as a voltage follower to pass the positive half cycle through to the output between resistors R15 and R17. The DC signal provided to the point between resistors R15 and R17 is always between 1.79 volts and the rail voltage of U2 and its magnitude represents the conductivity level of the fluid between points P7 and PS. Resistor R17 and capacitor C8 operate as a low pass filter to remove any short duration voltage spikes that may exist in the signal between resistors R15 and R17 at the output of amplifier U2.

Through the operation of the microprocessor U4 and the amplifier whose inverting input is connected to resistor R18 and R16, a delta-sigma technique can be used to determine the magnitude of conductivity of the fluid between points P7 and P8.

With continued reference to FIG. 13, the temperature of the fluid proximate the upper surface of the substrate can be measured by the use of a thermistor connected between points P9 and P10. In order to determine the resistance of the thermistor and, therefore, be able to determine the temperature of the fluid surrounding the present invention, output RA1 of the microprocessor U4 changes its state from 0 volts to VCC to provide that voltage potential at point P9. Because of the arrangement of capacitor C9 in combination with the thermistor, the voltage across capacitor C9 will change as a function of the time constant provided by the RC network. The voltage across capacitor C9 can be sensed by the RTCC input of microprocessor U4 which compares it to a predetermined threshold value. The time required to reach the predetermined threshold value is monitored by the microprocessor U4 and saved for the second step of the temperature measurement process. After the RTCC input of the microprocessor determines the time necessary to reach the threshold voltage level, the capacitor C9 is completely discharged. When the capacitor is discharged, output RA0 of microprocessor U4 provides a voltage potential at resistor R21. The voltage potential provided by output RA0 is identical to that provided by output RA1 during the first step of the process. Again, the RTCC input of microprocessor U4 monitors the voltage level at capacitor C9 and, when the capacitor voltage reaches the predetermined threshold magnitude, the time T2 is saved. Since the microprocessor U4 now knows times T1 and T2, and since resistor R21 has a known resistance value, the resistance of the thermistor between points P9 and P10 can be determined from the resulting time constance, the known capacitance of capacitor C9 and the known resistance of resistor R21 to solve the unknown resistance of the thermistor.

With continued reference to FIG. 13, the magnetically sensitive component U7 is a magnetoresistive device in a preferred embodiment of the present invention. Although it should be understood that, in certain circumstances, a Hall effect element could be used, the application of the present invention to a dishwasher results in a relatively large gap between the position of the magnet attached to the rotating arm and the position of the magnetically sensitive component U7. Therefore, in a preferred embodiment of the present invention, it was determined that a magnetoresistive element, such as permalloy should be used. The magnetically sensitive component U7 provides a digital signal to the RA3 input of microprocessor U4 whenever the magnet passes nearby.

Although many different types of circuits can be used in conjunction with the present invention and circuits similar to that shown in FIG. 13 could comprise various combinations of components and elements, Table I shows the component types and values of one particularly preferred embodiment of the present invention.

TABLE I

| REFERENCE | COMPONENT TYPE OR VALUE |
|---|---|
| R1 | 4.02K |
| R2 | 4.02K |
| R4 | 470 Ω |
| R5 | 470 Ω |
| R6 | 470 Ω |
| R7 | 1M |
| R8 | 7.5K |
| R9 | 4.02K |
| R10 | 1M |
| R11 | 20M |
| R12 | 20M |
| R13 | 3.3K |
| R14 | 28K |
| R15 | 28K |
| R16 | 100K |
| R17 | 8.2K |
| R18 | 56K |
| R19 | 18K |
| R20 | 180 Ω |
| R21 | 12K |
| R22 | 182K |
| R24 | 10K |
| R25 | 10K |
| R26 | |
| R27 | 2K |
| R28 | 150 Ω |

TABLE I-continued

| REFERENCE | COMPONENT TYPE OR VALUE |
|---|---|
| R29 | 100 Ω |
| R30 | 6.6K |
| R31 | 3.3K |
| R36 | 5.1K |
| R37 | 18K |
| R38 | 100K |
| R39 | 100K |
| R40 | 240K |
| R41 | 240K |
| R43 | 4.7K |
| R44 | 820 Ω |
| R45 | 2M |
| R46 | 10 Ω |
| C1 | 1 μF |
| C2 | .22 μF |
| C3 | 1 μF |
| C4 | .1 μF |
| C5 | 470 pF |
| C6 | 47 pF |
| C7 | .1 μF |
| C8 | .1 μF |
| C9 | .22 μF |
| C10 | .01 μF |
| C11 | .001 μF |
| C13 | .1 μF |
| C14 | .1 μF |
| C16 | .1 μF |
| C17 | .22 μF |
| C18 | .01 μF |
| C19 | .1 μF |
| U1 | 74HC4051DW (Motorola) |
| U2 | MC34074D (Motorola) |
| U3 | MC78L05ACD (Motorola) |
| U4 | PIC16C54-XT/SO (Microchip) |
| U5 | PBRC-4.00BR (AVX Kyocera) |
| U6 | TLC27M2CD (Texas Instruments) |
| U7 | 2SSP (Honeywell) |
| Q1 | 2N2907 (Motorola) |
| Q2 | 2N2222 (Motorola) |
| Q3 | 2N2222 (Motorola) |
| Q5 | BAV70LT1 (Motorola) |
| Q6 | BAV70LT1 (Motorola) |
| LED (P1-P2) | GL5UR3K (Sharp) |
| PHOTO-DIODE (P3-P4) (P5-P6) | VTB100 (EG & G Vactek) |
| THERMISTOR (P9-P10) | 135-LFW303-J01 (FENWALL) |

Figure 14:
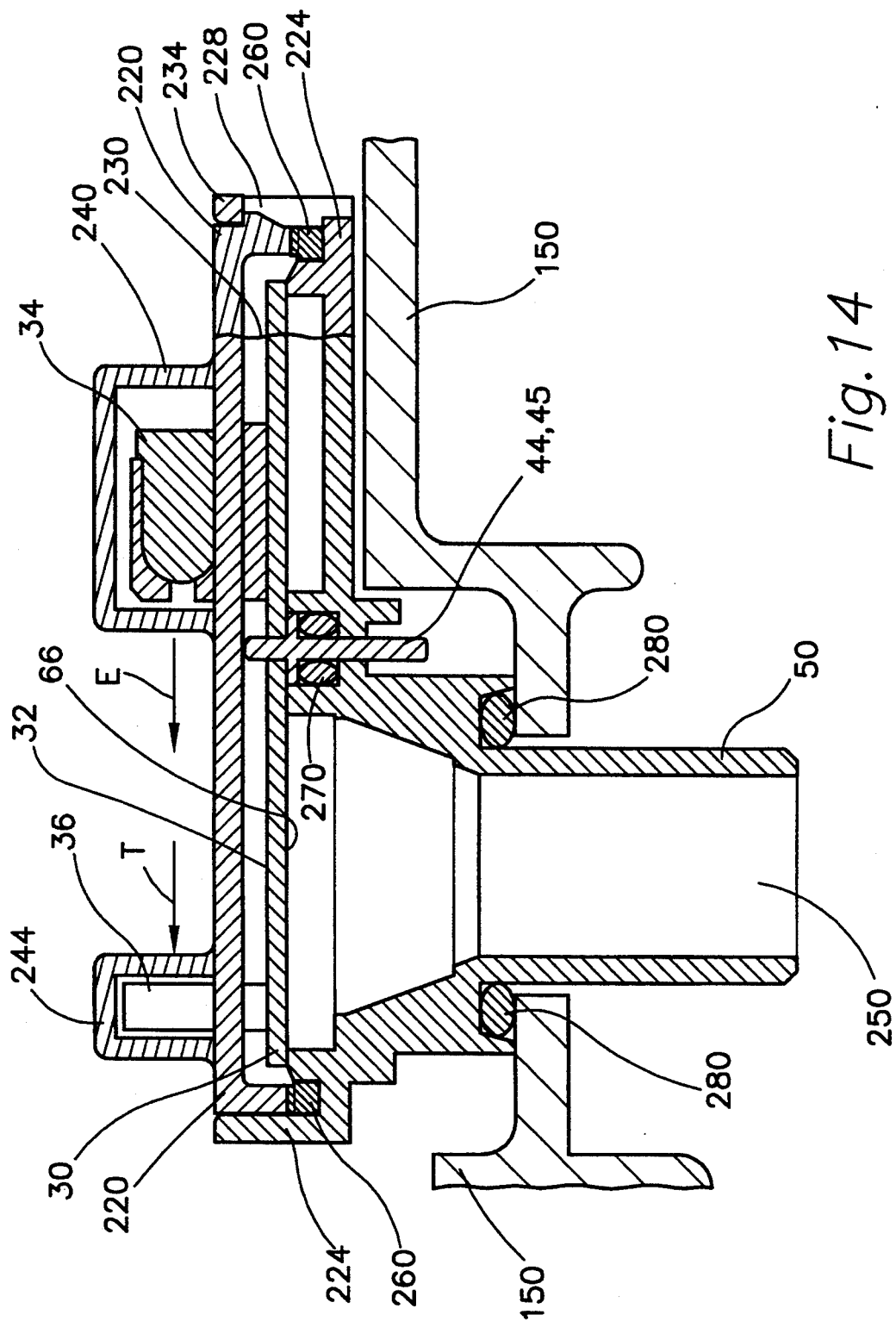
FIG. 14 illustrates an alternative embodiment of the present invention which utilizes a housing that comprises an upper and lower portion.

Although a preferred embodiment of the present invention encases the components of the sensor cluster within an overmolded material that is light transmissive and liquid impermeable, an alternative embodiment of the present invention can seal the components within a light transmissive and liquid impermeable case that comprises two parts. FIG. 14 illustrates this alternative embodiment of the present invention. Most of the components described above in conjunction with FIGS. 3, 4, 5, 6, 7, 8, 9 and 10 will not be discussed again in conjunction with FIG. 14, but those which are illustrated in FIG. 14 are identified by the same reference numerals.

Instead of an overmolded housing, the housing in FIG. 14 comprises an upper portion 220 and a lower portion 224. The upper portion 220 is shaped to be received within the lower portion 224 and the lower portion 224 is provided with a plurality of elastic fingers which snap into position to lock the upper portion 220 within the lower portion 224. A finger 228 is illustrated in the torn away section view to the right of line 230. The distal end 234 of the finger 228 snaps into position over preformed notches in the upper portion 220. The upper and lower portion are shaped to receive the substrate 30 therebetween as illustrated.

The embodiment shown in FIG. 14 differs from that shown in FIG. 3 because the pins, 44 and 45, extend downward from the substrate 30 instead of upward as shown in FIG. 3. It should be understood that this configuration with regard to the conductive pins is chosen for a particular application and is not limiting to the present invention.

The upper portion 220 of the housing structure is shaped to have protrusions in its upper surface to receive the light emitting and light receiving components described above. A first protrusion 240 is shaped to receive the light emitting diode 34 and a second protrusion 244 is shaped to receive the light sensitive component 36. Although not shown in FIG. 14, it should be understood that a similar protrusion would be shaped to receive the other light sensitive component 40.

In FIG. 14, the conductors 58 and the connector 67 are not illustrated for purposes of simplicity. However, it should be understood that the conductor 58 would extend through the opening 250 of the sensor cluster. In order to protect the component on the first and second surfaces of the substrate 30, the upper and lower portions of the housing are attached to each other in a liquid impermeable manner that utilizes seals 260, 270 and 280. Seal 260 is compressed between the associated surfaces by the force provided by the fingers 228 and their distal ends 234. The seals shown in FIG. 14 are exemplary and could be replaced by alternative methods of preventing liquid from penetrating into the cavity between the upper and lower housing portions.

It should be understood that FIGS. 4 and 14 represent two alternative embodiments of the same invention. The embodiments shown in FIG. 4 utilizes an overmolded coating of a material that is light transmissive and liquid impermeable. The embodiment shown in FIG. 14 utilizes an upper housing portion and a lower housing portion that combine to seal the electronic components therebetween. The selection of one of these two embodiments over the other depends on the application and the structure of the substrate and components that are to be protected from a surrounding liquid environment.

Although the present invention has been described in considerable detail and illustrated with a high degree of specificity, it should be understood that alternative embodiments are within its scope.

The embodiments of the invention in which an exclusive property or right is claimed are defined as follows:

1. A sensor, comprising:
   a light source disposed to transmit a beam of light in a direction along a first line through a detection zone;
   a first light sensor disposed to receive light transmitted along said first line from said light source, said first light sensor providing a first signal representative of the intensity of light impinging on said first light sensor;
   a second light sensor disposed to receive light from said light source which is scattered along a second line, said second light sensor providing a second signal representative of the intensity of light impinging on said second light sensor, said second line extending at a first angle from said first line;
   means for selecting the highest one of said first and second signals; and
   a regulator for controlling the intensity of light emanating from said light source as a function of said highest one of said first and second signals, said regulator comprising an amplifier, said highest one of said first and second signals being connected in signal communication with an input of said amplifier, another input of said amplifier being connected in signal communication with a reference voltage, said reference voltage being selected to represent a maximum allowable level of said highest one of said first and second signals.

2. The sensor of claim 1, wherein:
   said sensor is a turbidity sensor.

3. The sensor of claim 1, wherein:
   said sensor is disposed within a machine for washing articles.

4. A sensor, comprising:
   a light source disposed to transmit a beam of light in a direction along a first line through a detection zone;
   a first light sensor disposed to receive light transmitted along said first line, said first light sensor providing a first signal representative of the intensity of light impinging on said first light sensor;
   a second light sensor disposed to receive light scattered along a second line, said second light sensor providing a second signal representative of the intensity of light impinging on said second light sensor, said second line extending at an angle from said first line; and
   a regulator for continuously controlling the intensity of said light source as a function of the highest one of said first and second signals, said regulator comprises an amplifier, said highest one of said first and second signals being connected in signal communication with an input of said amplifier, another input of said amplifier being connected in signal communication with a reference voltage.

5. The sensor of claim 4, wherein:
   said sensor is a turbidity sensor.

6. The sensor of claim 5, wherein:
   said turbidity sensor is disposed within a machine for washing articles.

7. The sensor of claim 6, wherein:
   said reference voltage is selected as a function of a saturation level of said first and second signals.

8. A sensor, comprising:
   a light source disposed to transmit a beam of light in a direction along a first line through a detection zone;
   a first light sensor disposed to receive light transmitted along said first line, said first light sensor providing a first signal representative of the intensity of light impinging on said first light sensor;
   a second light sensor disposed to receive light scattered along a second line, said second light sensor providing a second signal representative of the intensity of light impinging on said second light sensor, said second line extending at an angle from said first line; and
   a regulator for controlling the intensity of light emanating from said light source as a function of a highest one of said first and second signals, said sensor being a turbidity sensor said regulator comprising an amplifier, said highest one of said first and second signals being connected in signal communication with an inverting input of said amplifier, a noninverting input of said amplifier being connected in signal communication with a reference voltage.

9. The sensor of claim 8, wherein:
   said sensor is disposed within a machine for washing articles.

10. The sensor of claim 8, wherein:
    said reference voltage is selected as a function of a saturation level of said first and second signals.

* * * * *